US010888620B2

(12) United States Patent
McNally et al.

(10) Patent No.: US 10,888,620 B2
(45) Date of Patent: Jan. 12, 2021

(54) LIQUID COMPOSITIONS FOR TREATING COUGH OR COLD SYMPTOMS

(71) Applicant: Johnson & Johnson Consumer Inc., Skillman, NJ (US)

(72) Inventors: Gerard P. McNally, Glenside, PA (US); Anurag Pandey, Lafayette Hill, PA (US); Vipul Dave, Hillsborough, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 152 days.

(21) Appl. No.: 15/824,301

(22) Filed: Nov. 28, 2017

(65) Prior Publication Data
US 2018/0147285 A1    May 31, 2018

Related U.S. Application Data

(60) Provisional application No. 62/427,080, filed on Nov. 28, 2016.

(51) Int. Cl.
| | |
|---|---|
| *A61K 9/08* | (2006.01) |
| *A61P 11/04* | (2006.01) |
| *A61K 47/38* | (2006.01) |
| *A61K 47/10* | (2017.01) |
| *A61K 47/34* | (2017.01) |
| *A61P 11/14* | (2006.01) |
| *A61P 11/00* | (2006.01) |
| *A61K 31/09* | (2006.01) |
| *A61K 31/137* | (2006.01) |
| *A61K 31/167* | (2006.01) |
| *A61K 31/192* | (2006.01) |
| *A61K 31/485* | (2006.01) |
| *A61K 47/26* | (2006.01) |
| *A61K 47/32* | (2006.01) |

(52) U.S. Cl.
CPC ............... *A61K 47/38* (2013.01); *A61K 9/08* (2013.01); *A61K 31/09* (2013.01); *A61K 31/137* (2013.01); *A61K 31/167* (2013.01); *A61K 31/192* (2013.01); *A61K 31/485* (2013.01); *A61K 47/10* (2013.01); *A61K 47/26* (2013.01); *A61K 47/32* (2013.01); *A61K 47/34* (2013.01); *A61P 11/00* (2018.01); *A61P 11/04* (2018.01); *A61P 11/14* (2018.01)

(58) Field of Classification Search
CPC ........ A61K 47/38; A61K 9/0095; A61K 9/08; A61K 31/09; A61K 31/167; A61K 47/10; A61P 11/04; A61P 11/14; A61P 11/00
See application file for complete search history.

(56) References Cited

U.S. PATENT DOCUMENTS

| | | | |
|---|---|---|---|
| 4,226,848 A * | 10/1980 | Nagai | A61K 9/0043 424/435 |
| 4,906,478 A | 3/1990 | Valentine et al. | |
| 5,275,822 A | 1/1994 | Valentine et al. | |
| 5,571,533 A * | 11/1996 | Santus | A61K 9/1617 424/469 |
| 6,103,260 A | 8/2000 | Luber et al. | |
| 8,342,032 B2 | 1/2013 | Debon et al. | |
| 8,413,481 B2 | 4/2013 | Debon et al. | |
| 8,541,026 B2 * | 9/2013 | Qiu | A61K 9/2077 424/468 |
| 2003/0113377 A1 * | 6/2003 | Dobrozsi | A61K 9/0056 424/486 |
| 2004/0185093 A1 | 9/2004 | Szymczak | |
| 2006/0062811 A1 | 3/2006 | Szymczak | |
| 2011/0195042 A1 * | 8/2011 | Huetter | A61K 9/006 424/78.32 |

FOREIGN PATENT DOCUMENTS

| | | |
|---|---|---|
| EP | 0506563 B1 | 1/1995 |
| WO | WO 92/07559 A1 | 5/1992 |
| WO | WO 95/23591 A1 | 9/1995 |
| WO | WO 2002/064113 A1 | 8/2002 |
| WO | WO 2013/049539 A1 | 4/2003 |
| WO | WO 2007/110871 A2 | 10/2007 |

OTHER PUBLICATIONS

Batchelor, Hannah et al; "The application of tribology in assessing texture perception of oral liquid medicines". International Journal of Pharmaceutics, Elsevier, Amsterdam, NL, vol. 479, No. 2, Jan. 6, 2015, pp. 277-281.
Prakash, Sangeeta et al; Application of tribology in studying food oral processing and texture perception, Food Research International, vol. 54, No. 2, Dec. 31, 2013, pp. 1627-1635.
International Search report for PCT/US2017/063434 dated Mar. 7, 2018.

* cited by examiner

*Primary Examiner* — Theodore R. West

(57) ABSTRACT

Compositions useful in the treatment of cough and cold symptoms, including but not limited to, cough, nasal congestion and sore throat, are disclosed.

11 Claims, 20 Drawing Sheets

Stribeck curve

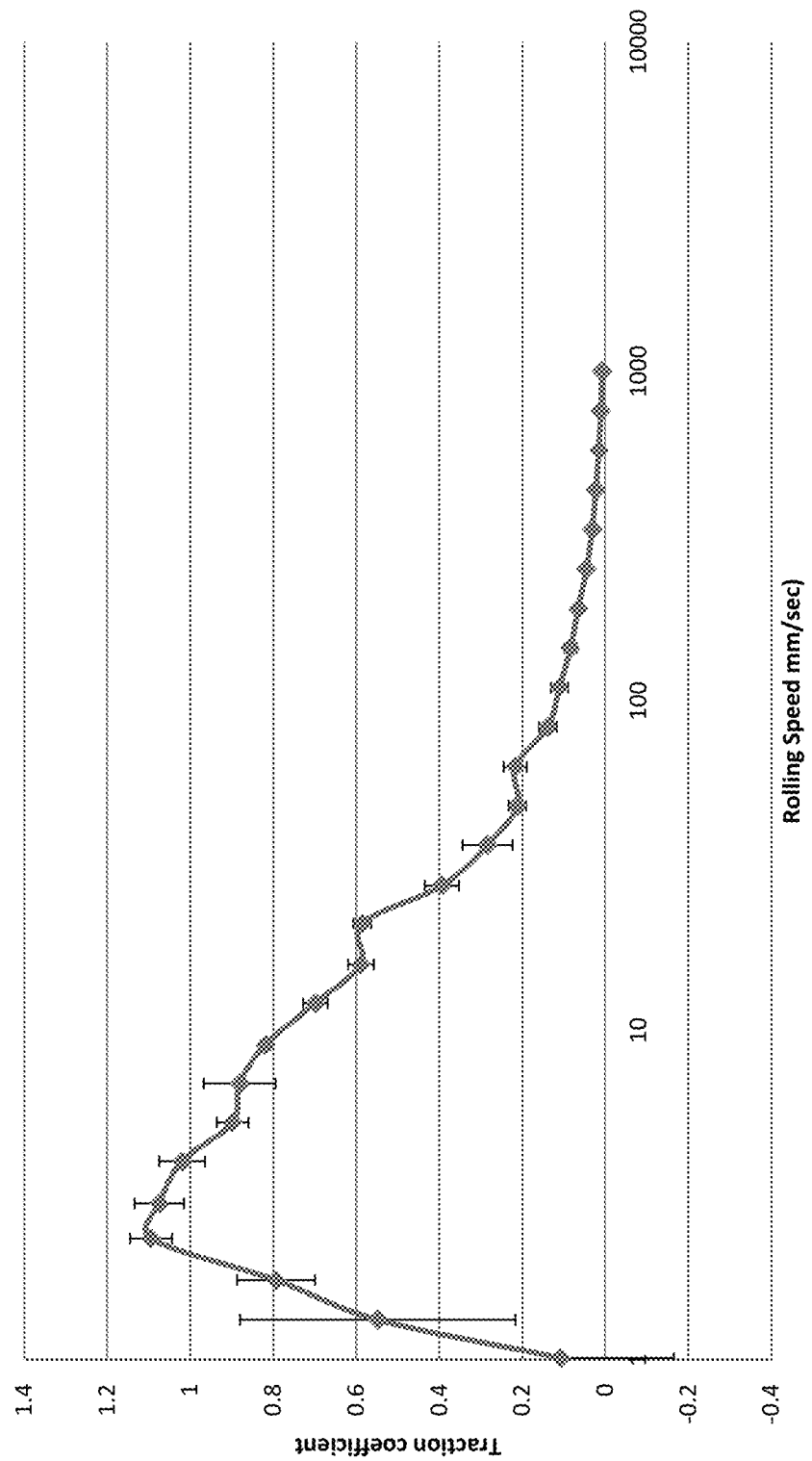

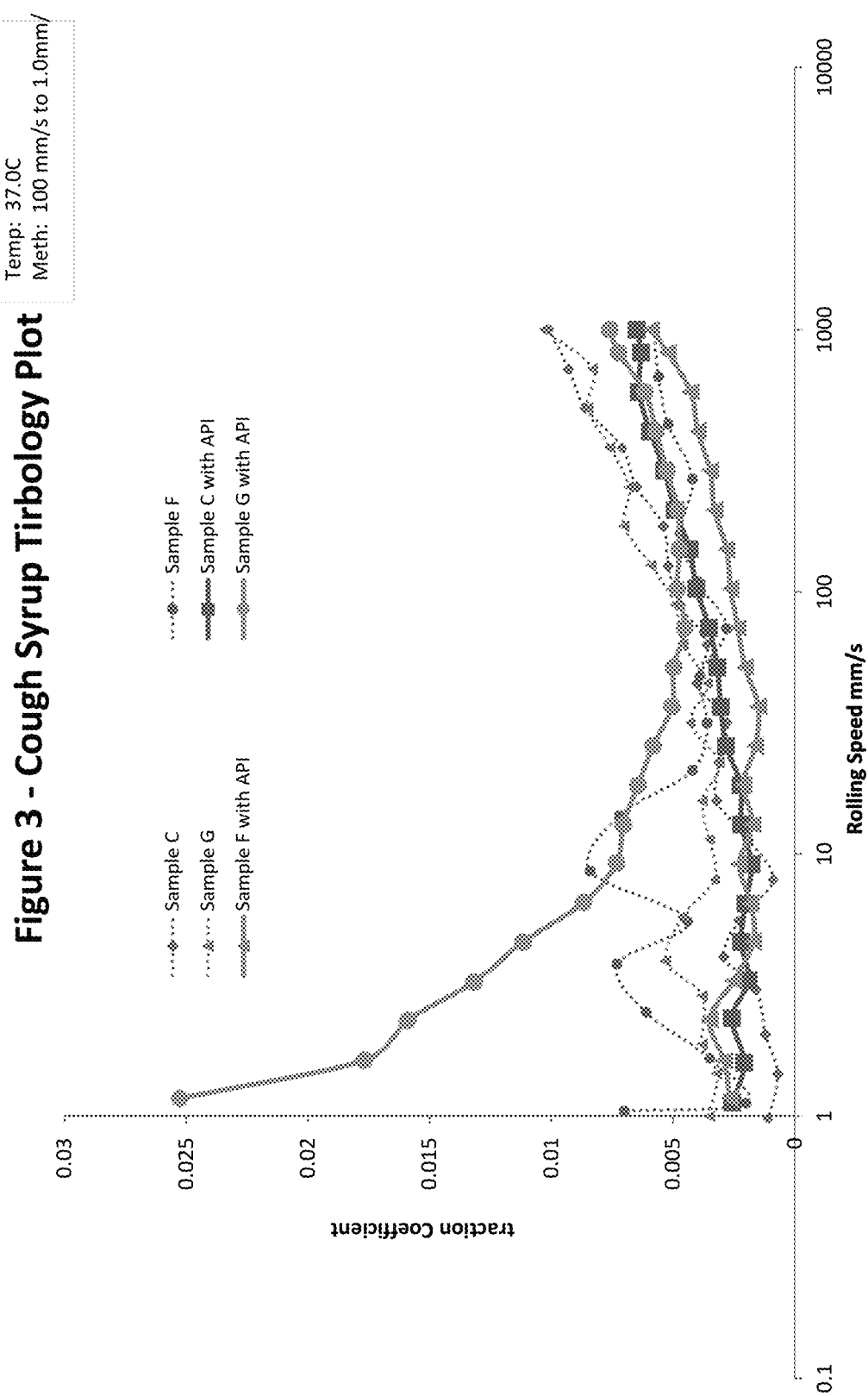

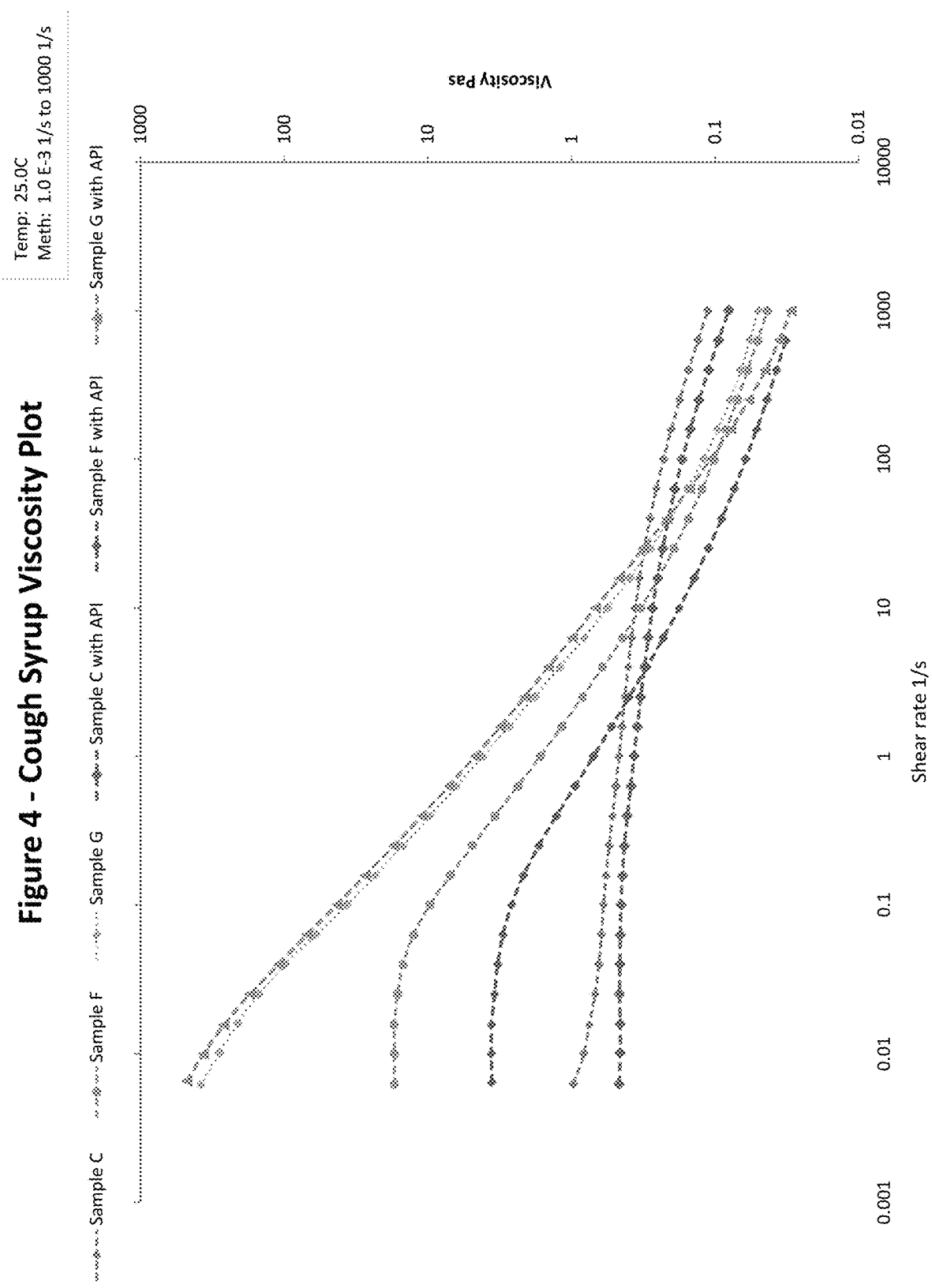

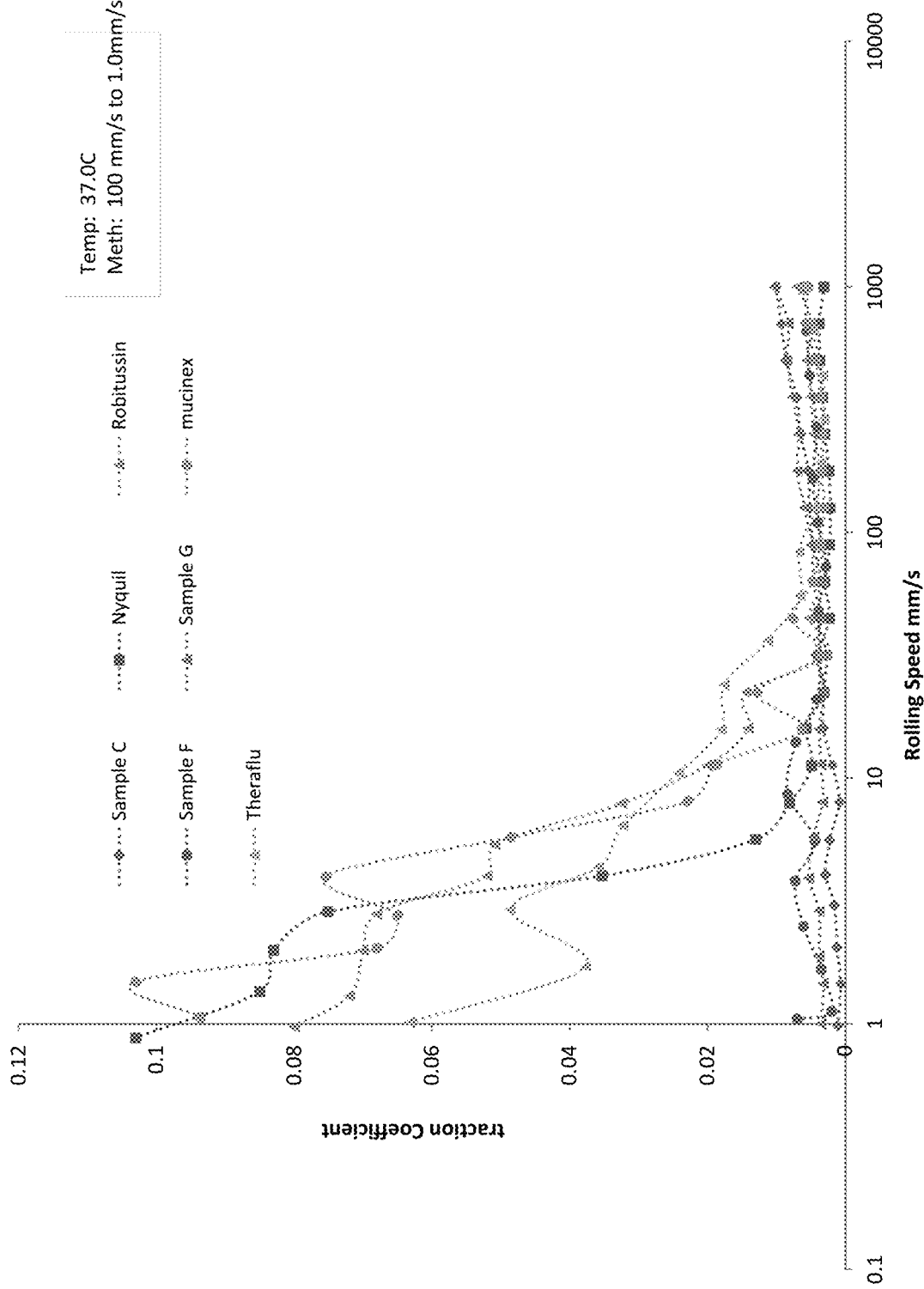

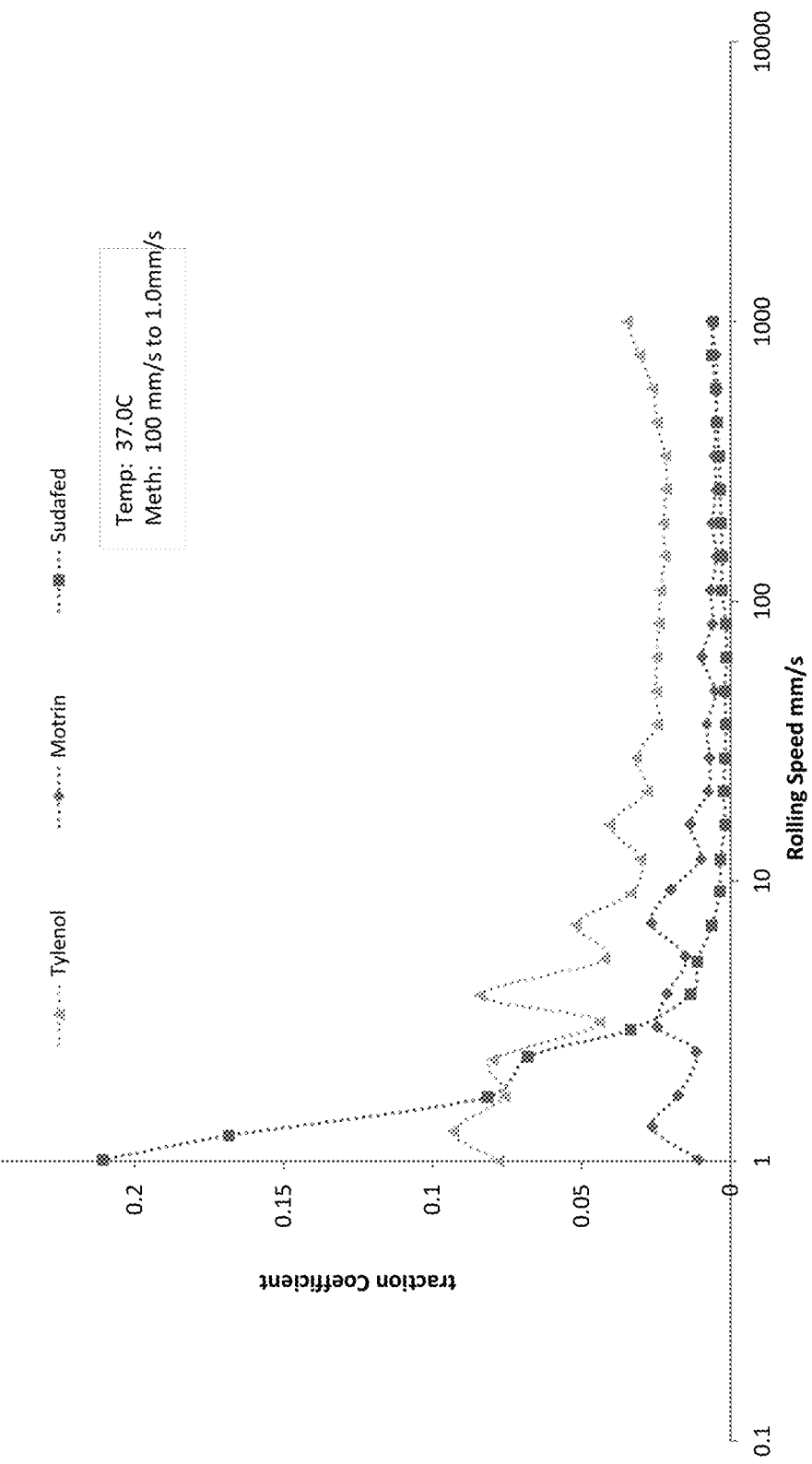

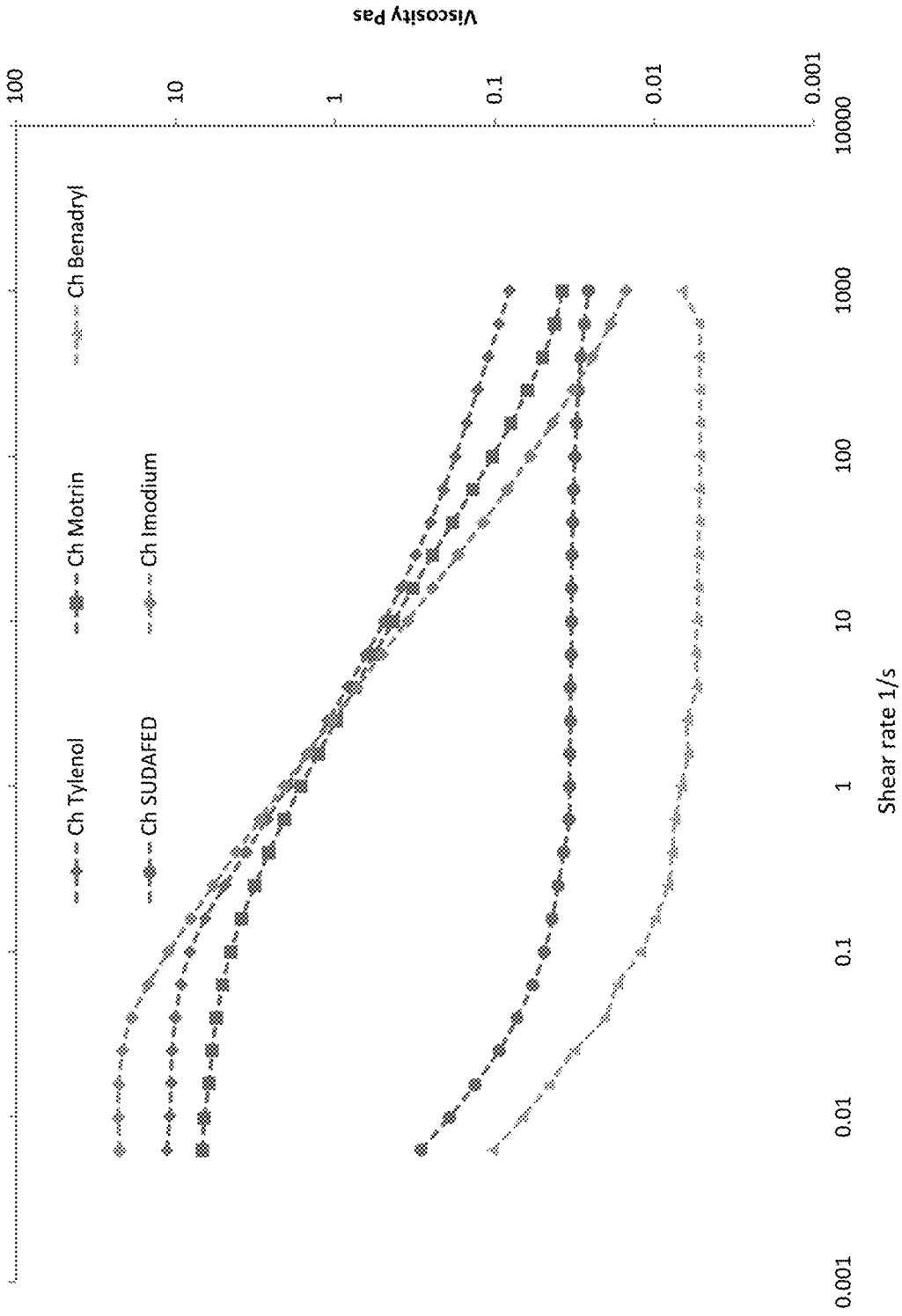
Figure 7 - Pediatric Drug Viscosity Plot

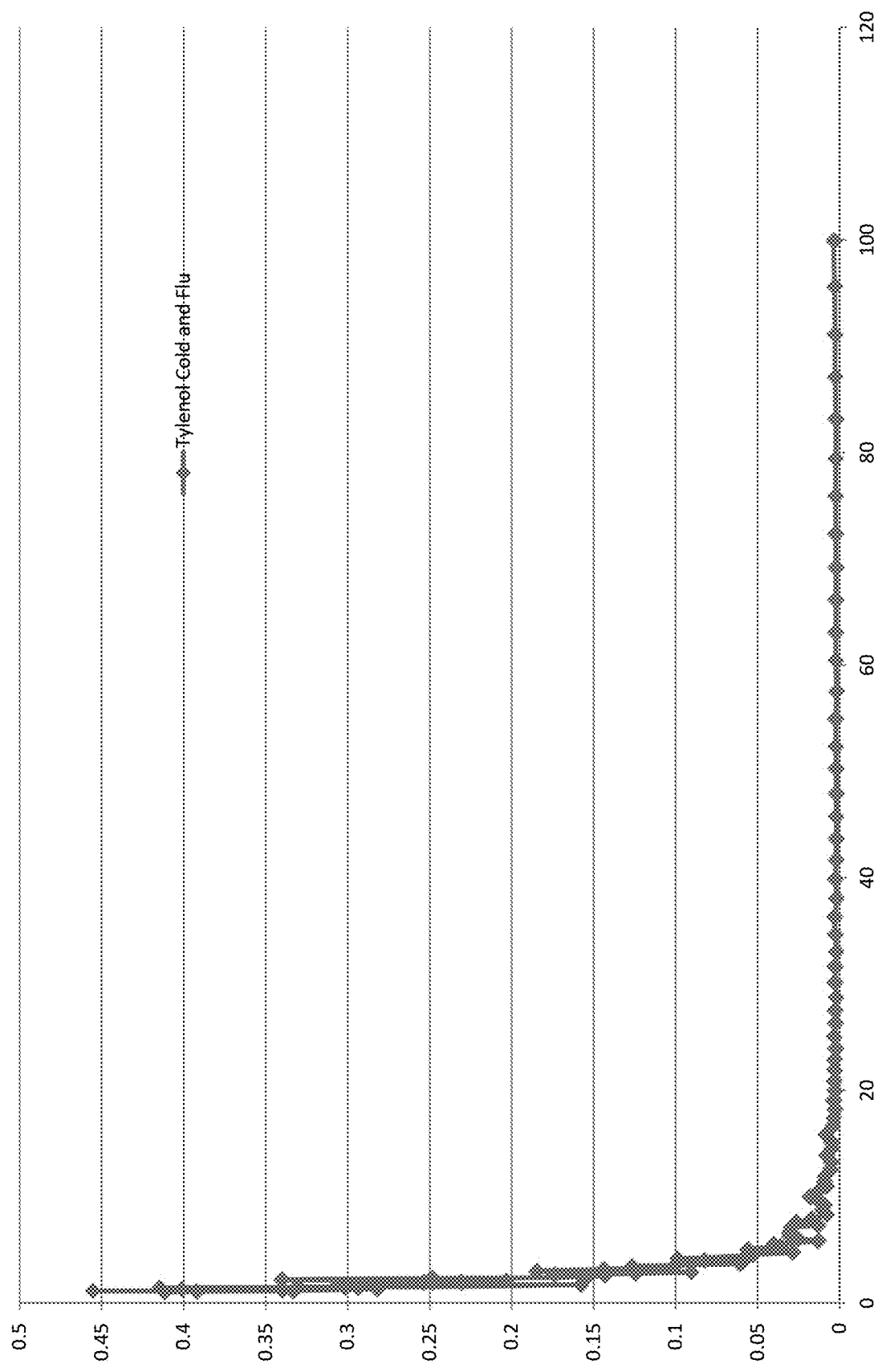
Figure 8 - Tylenol Cold and Flu

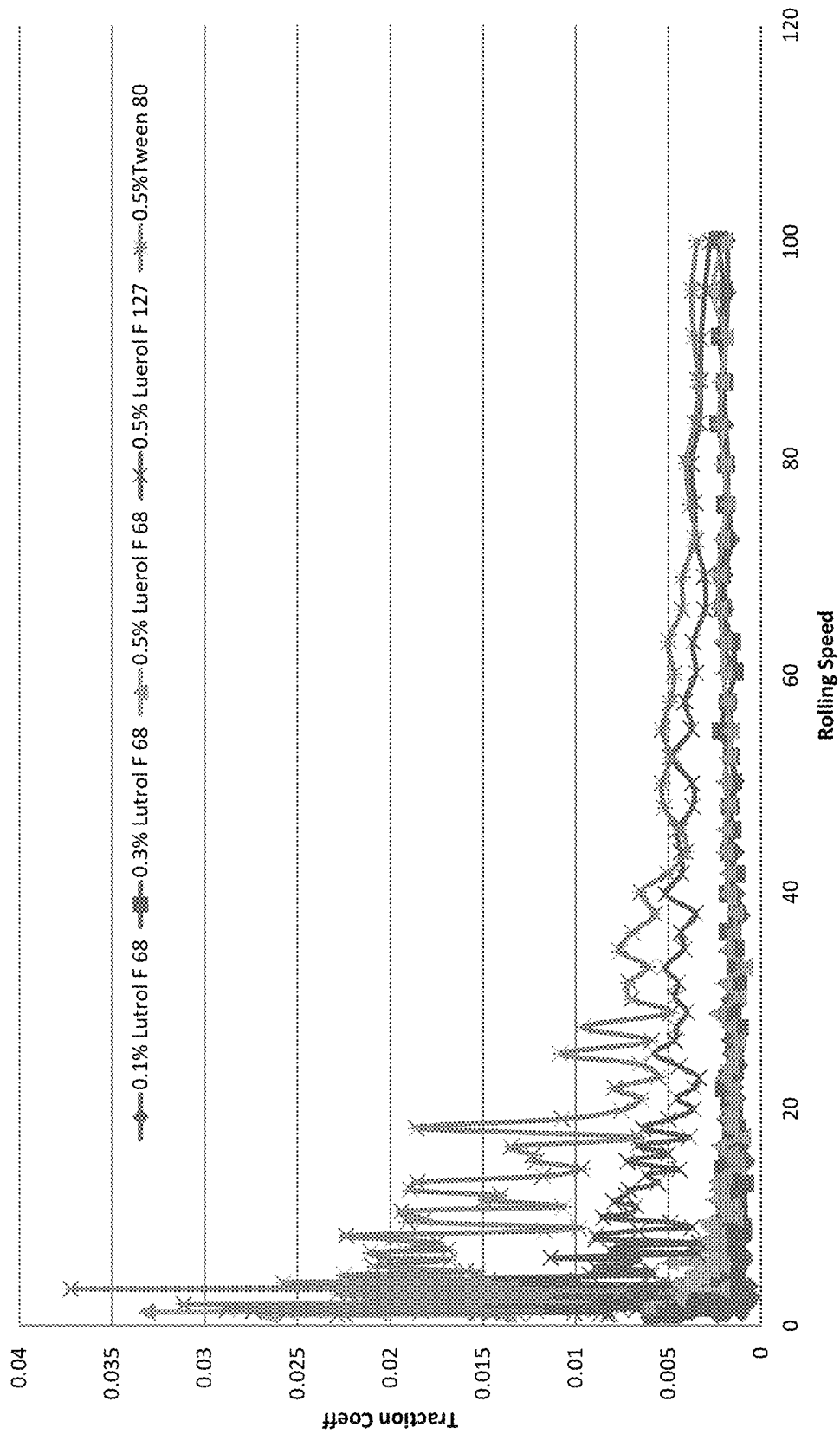

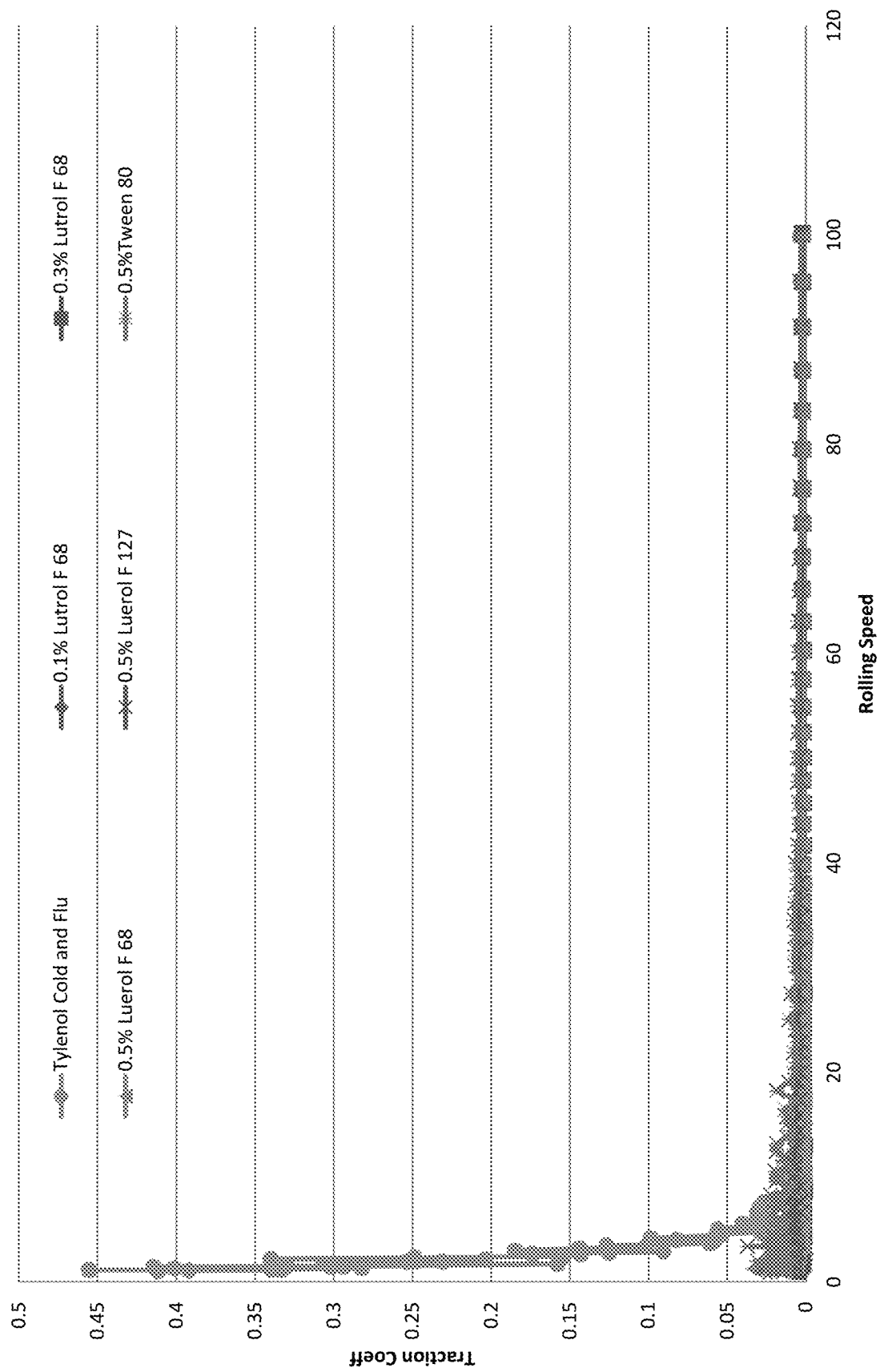

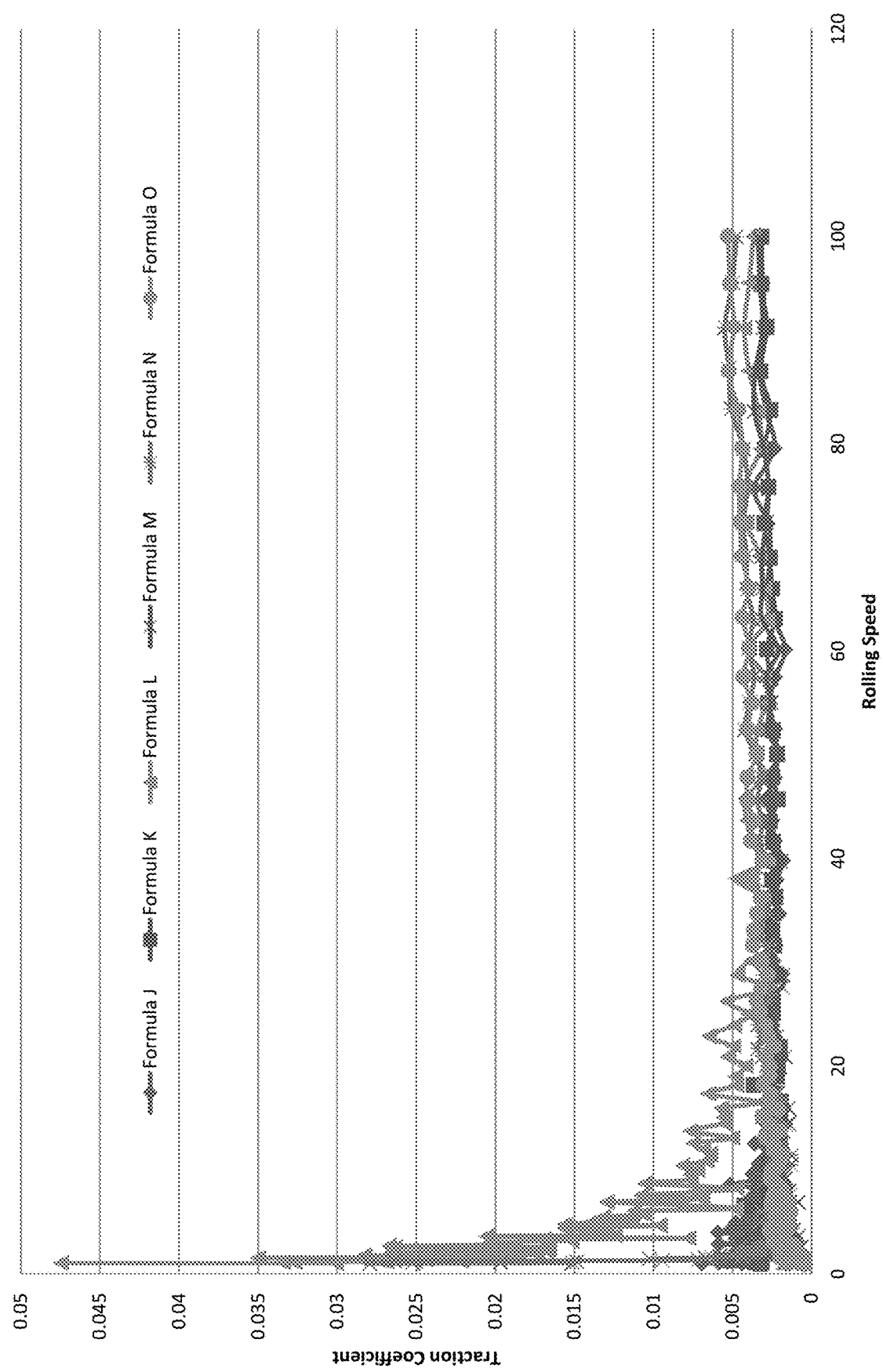

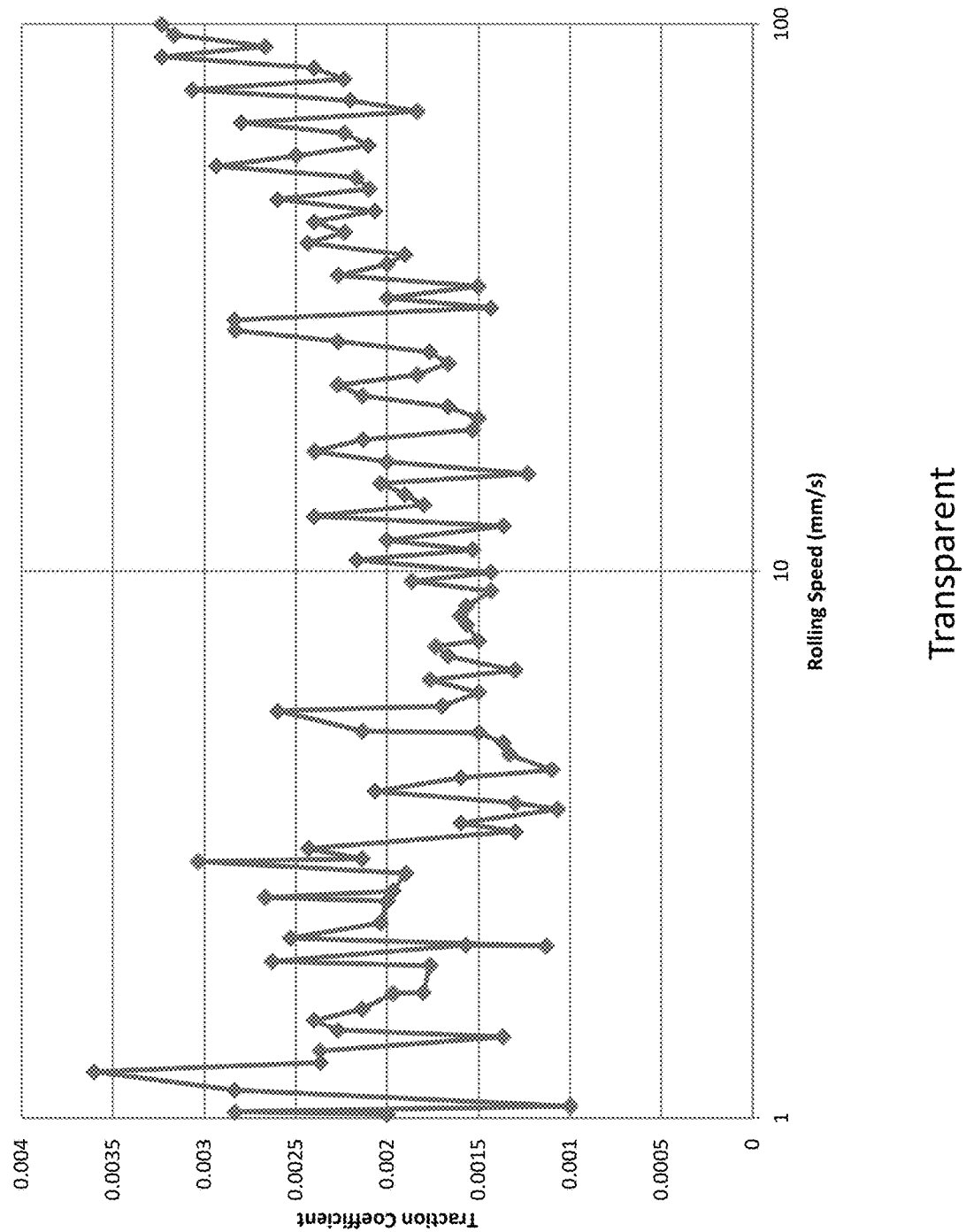

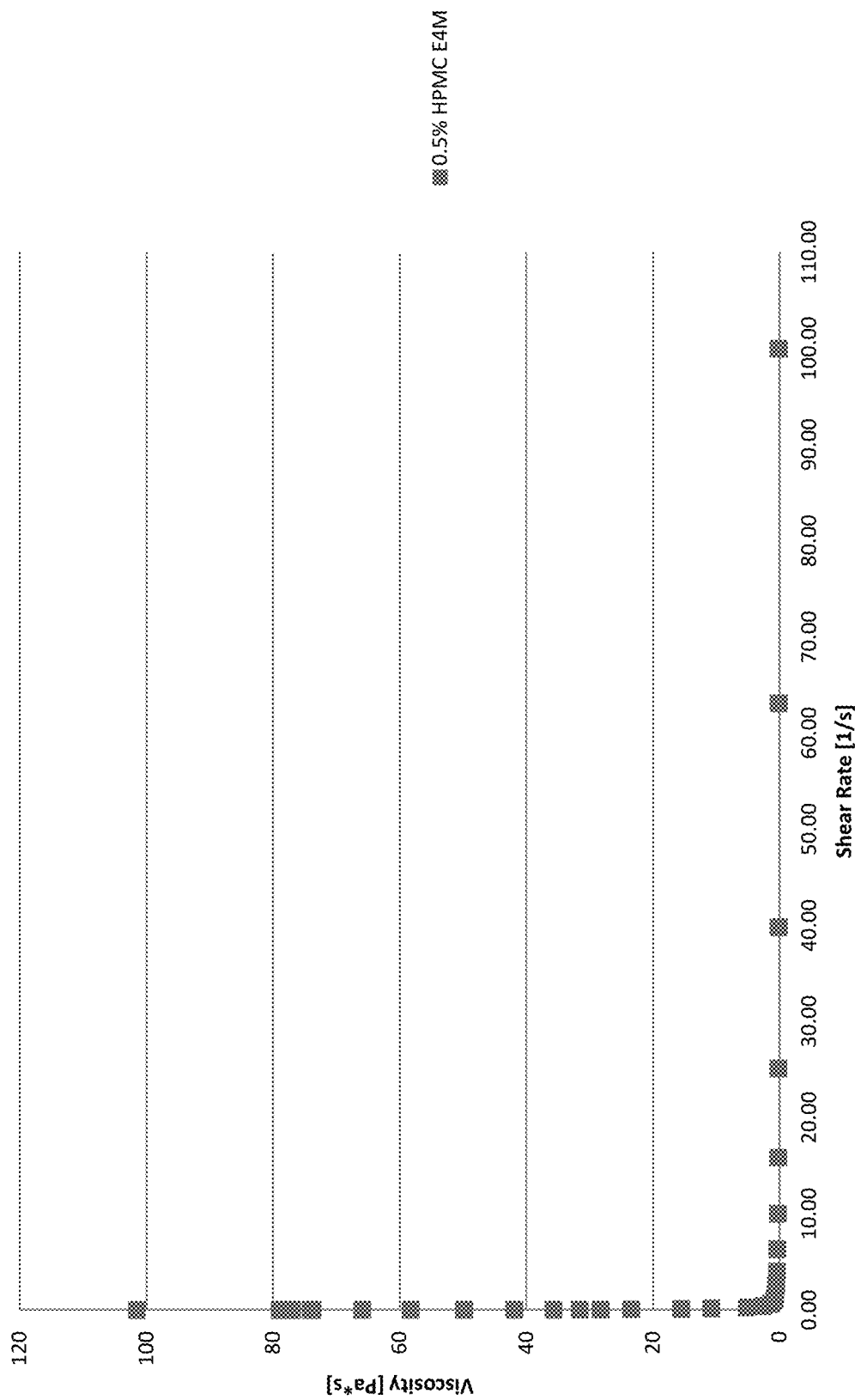

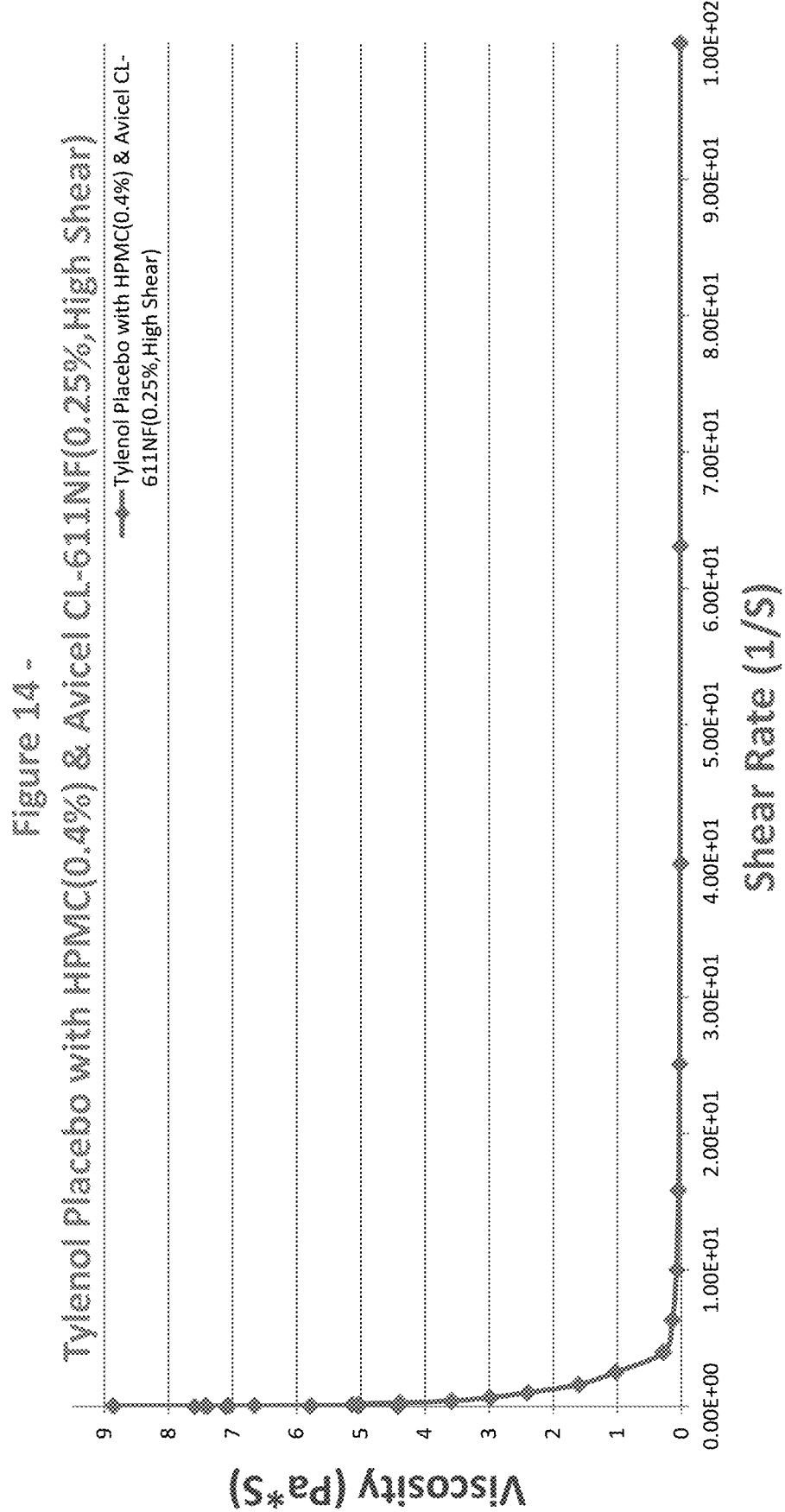
Figure 14 - Tylenol Placebo with HPMC(0.4%) & Avicel CL-611NF(0.25%, High Shear)

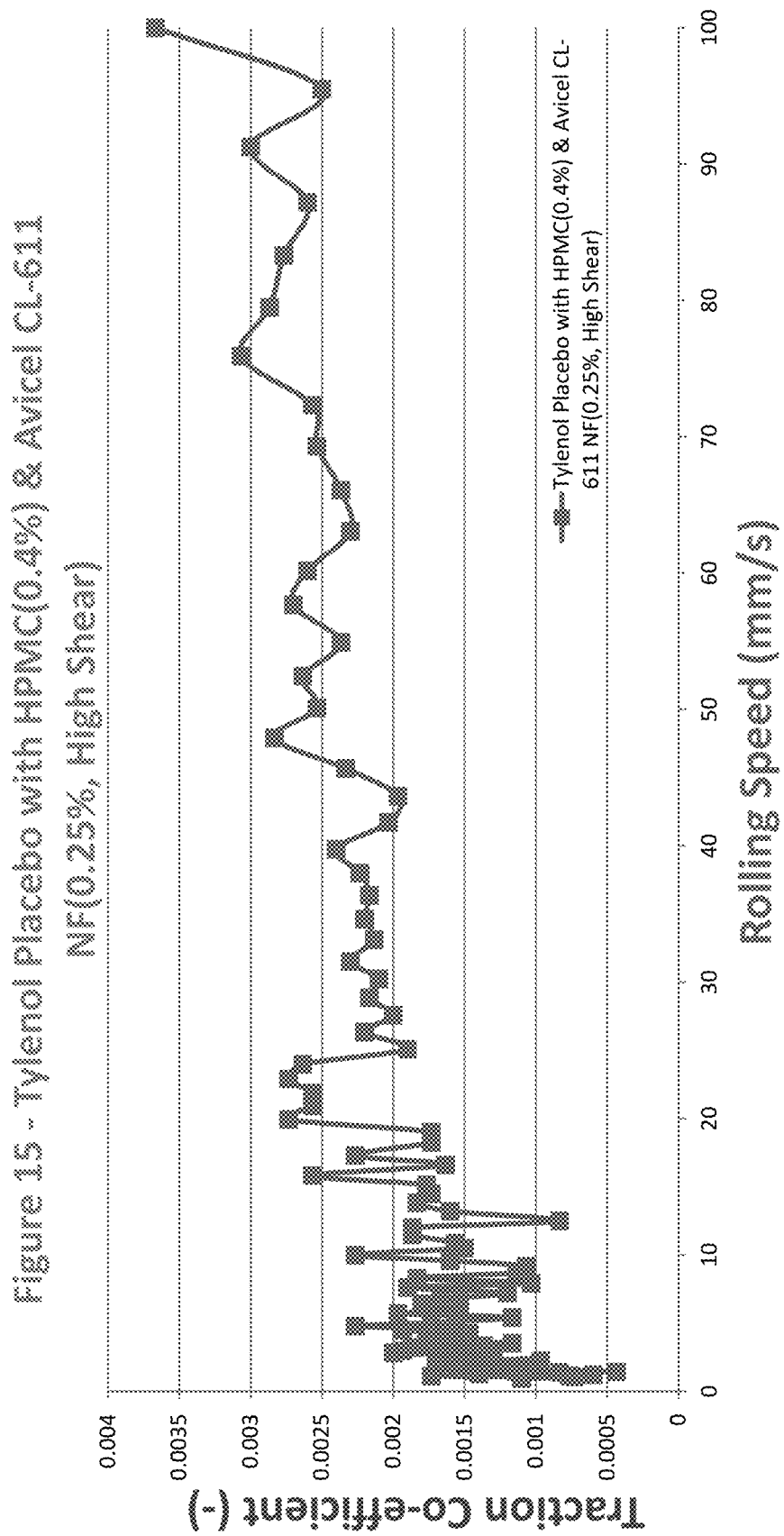

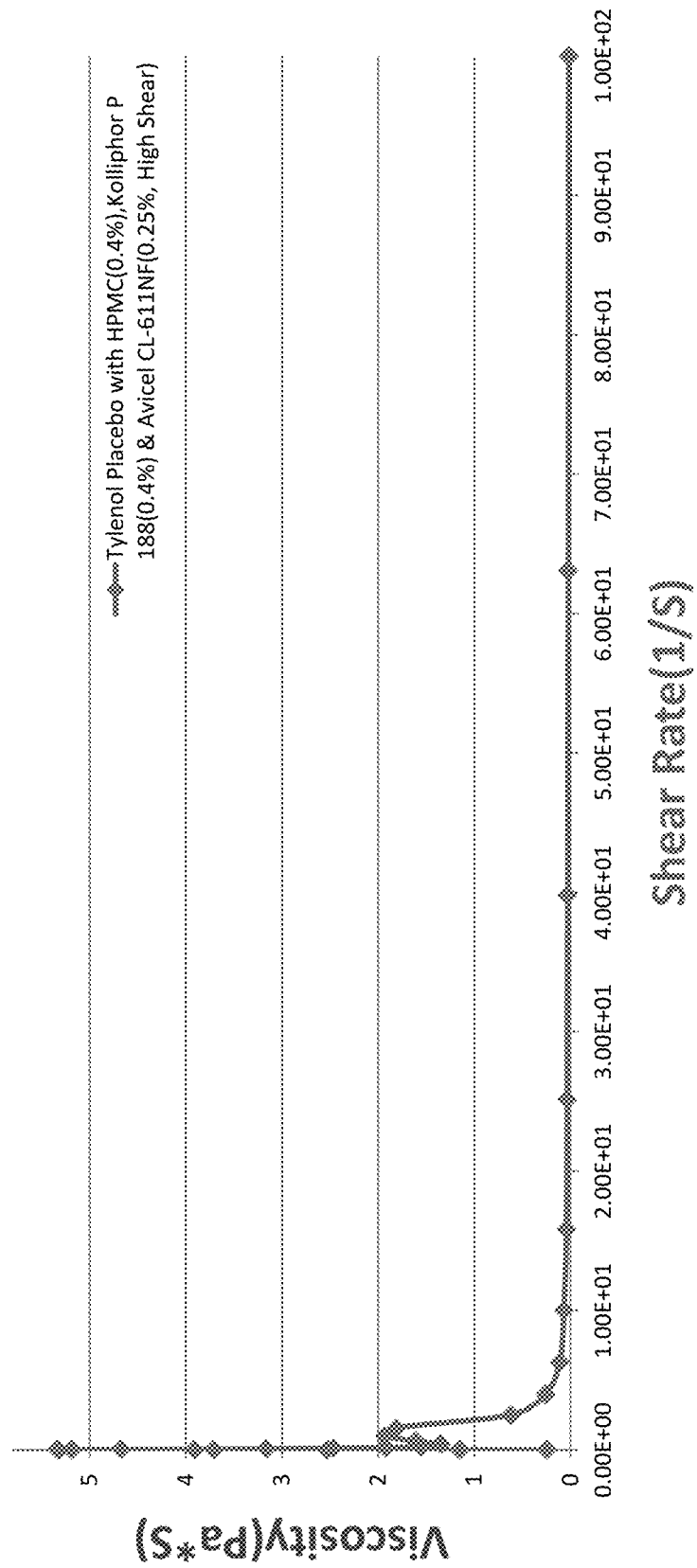

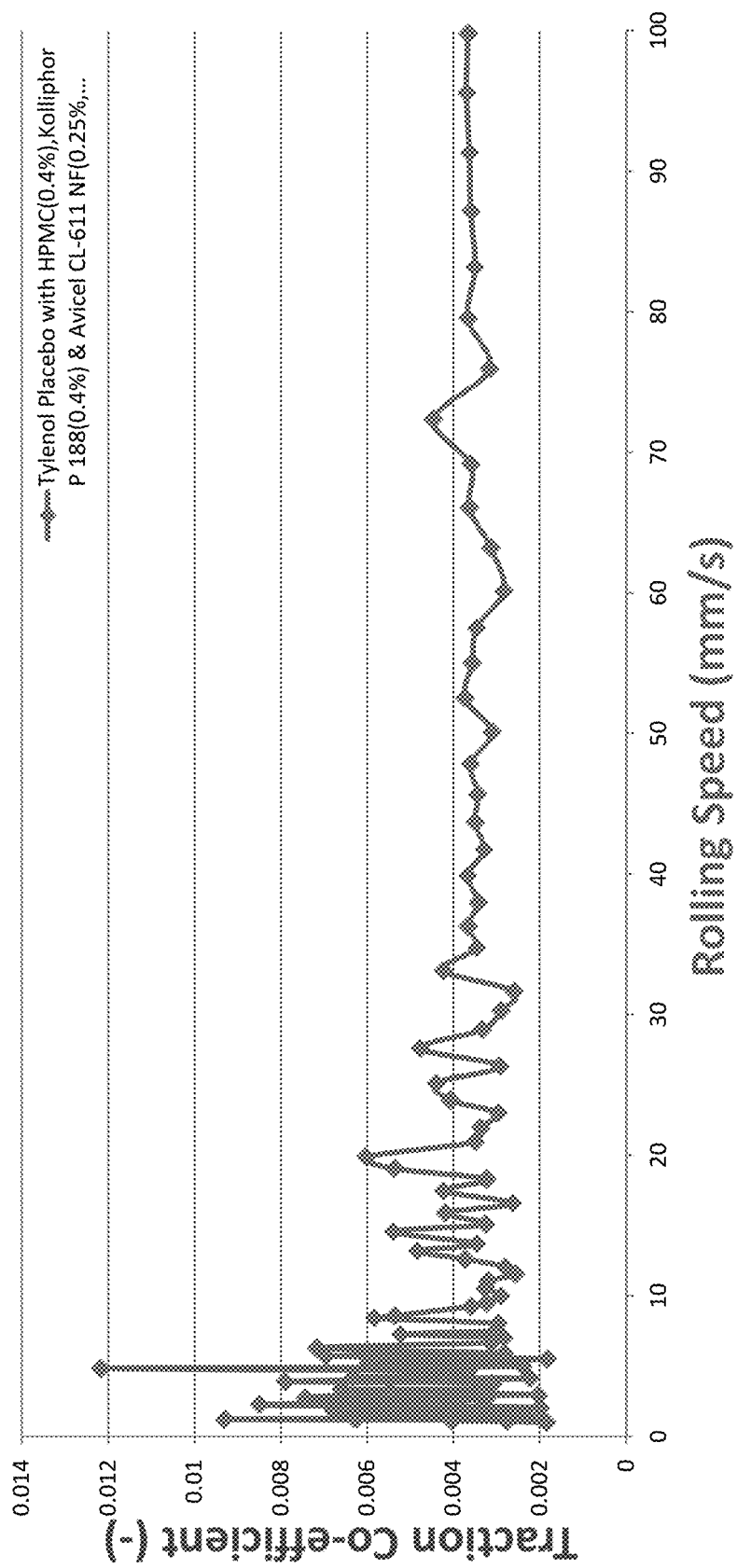

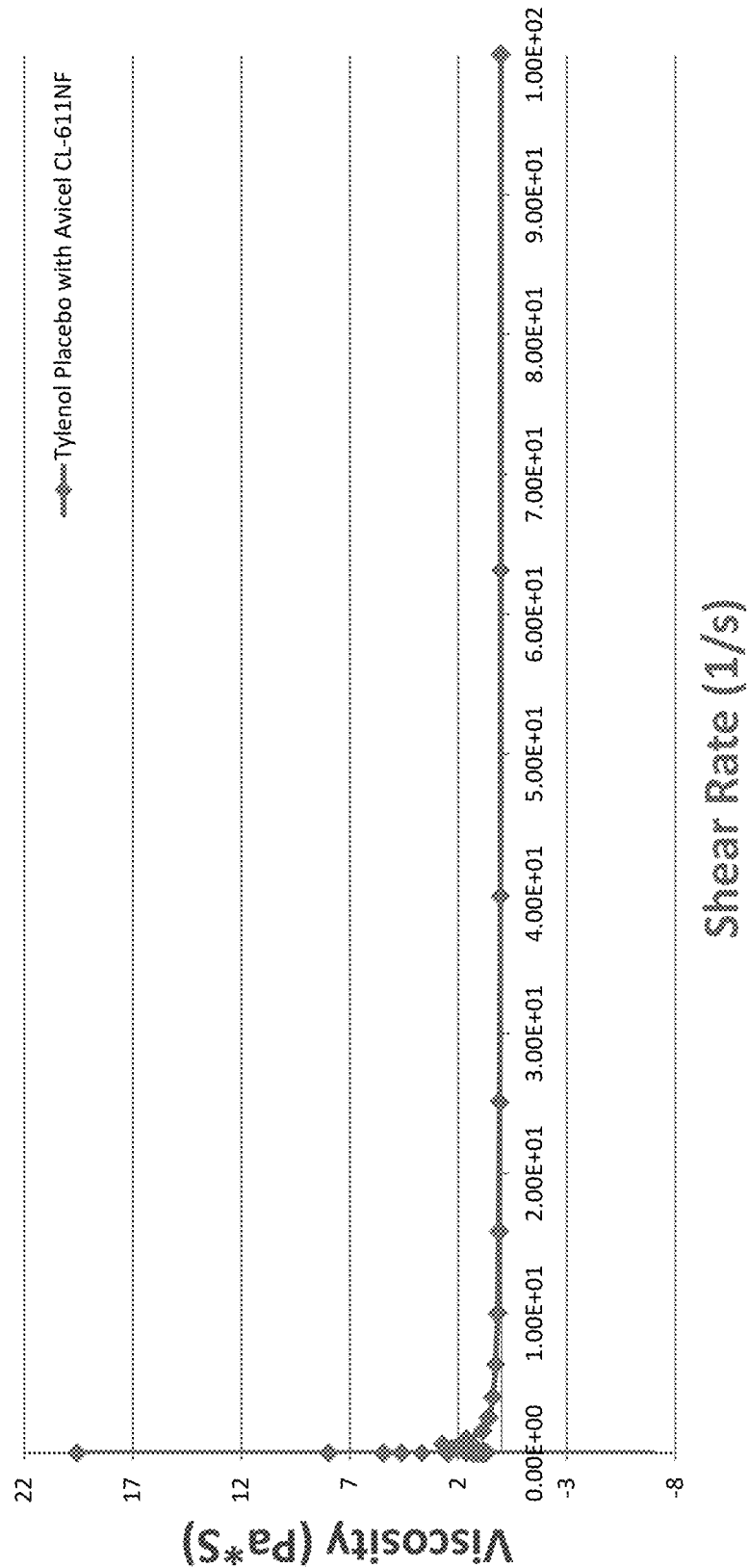

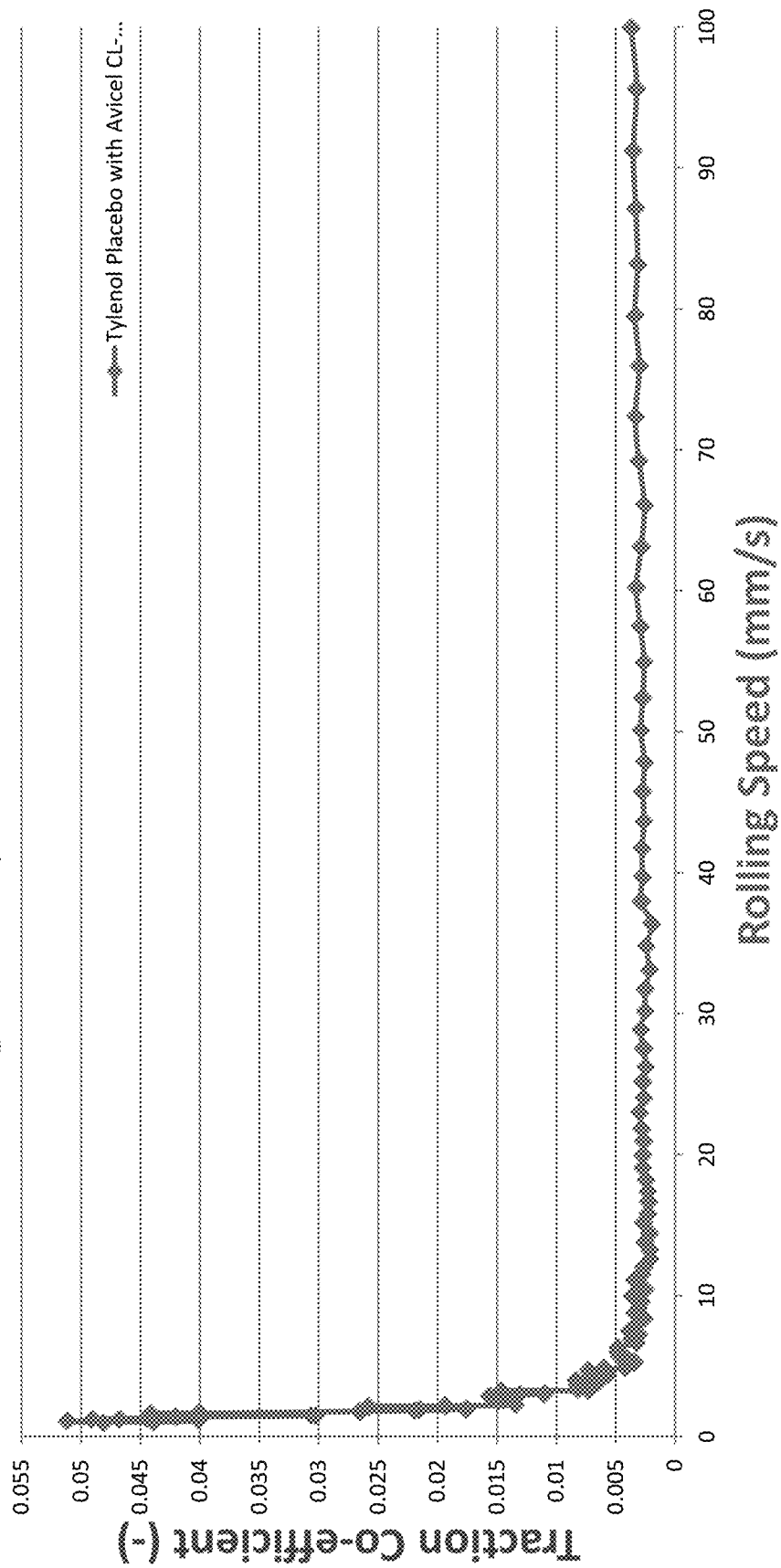

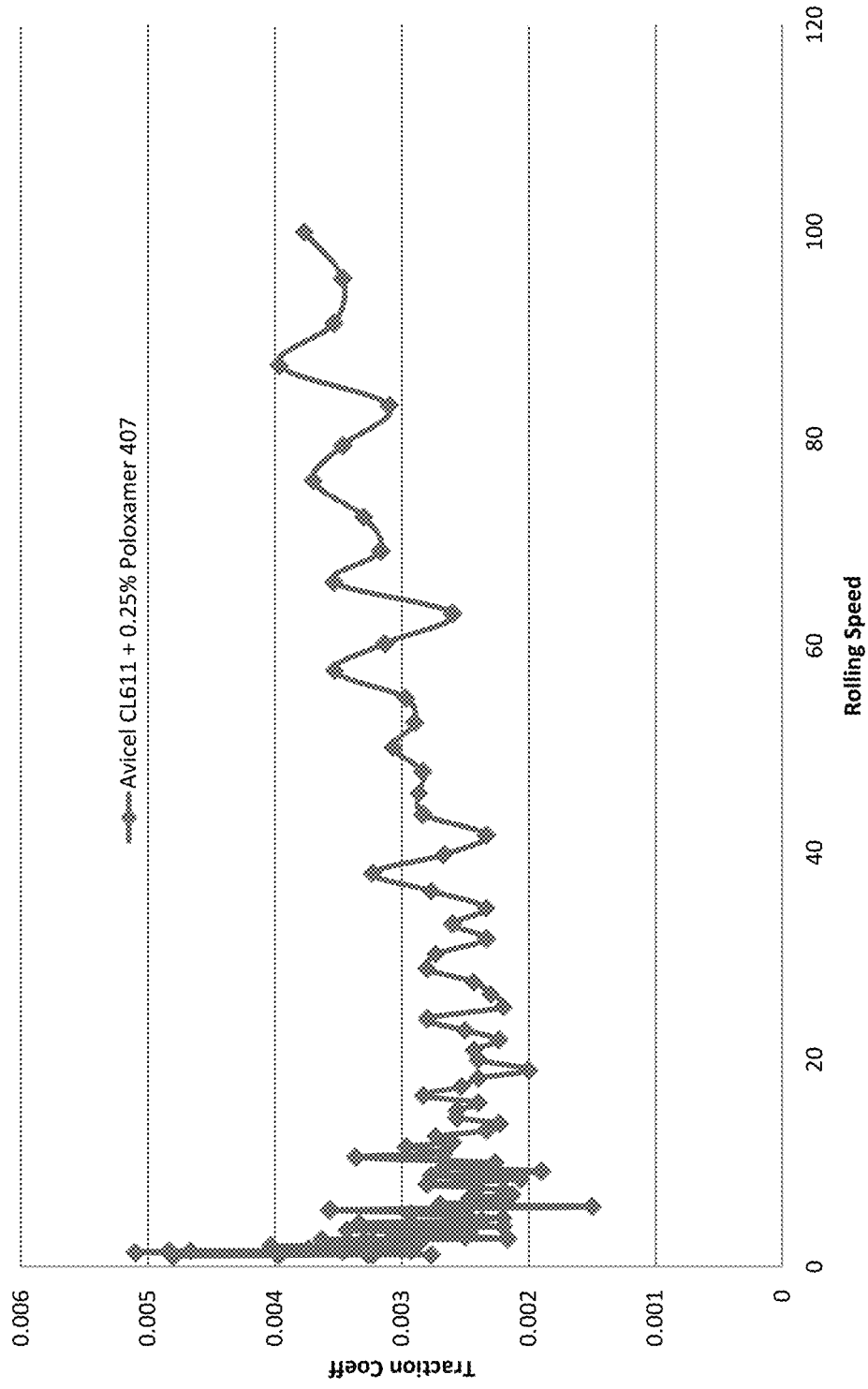

LIQUID COMPOSITIONS FOR TREATING COUGH OR COLD SYMPTOMS

CROSS REFERENCE TO RELATED APPLICATIONS

This application claims priority of the benefits of U.S. Provisional Application Ser. No. 62/427,080, filed Nov. 28, 2016. The complete disclosure of the aforementioned related U.S. patent application is hereby incorporated by reference for all purposes.

FIELD OF THE INVENTION

The present invention relates to liquid compositions. The present invention also relates to a process for manufacturing the liquid compositions and to methods for alleviating symptoms in human subjects upon administration of the liquid compositions. The liquid compositions, which can comprise one or more therapeutically active agents, are particularly useful in treatment of cough and cold symptoms, including but not limited to, cough, nasal congestion and sore throat.

BACKGROUND OF THE INVENTION

A sore throat is characterized by a pain or irritation of the throat or pharynx, usually caused by acute pharyngitis. A sore throat is most often caused by a viral infection. A sore throat can also be caused by a streptococcal infection, tumors, gastroesophageal reflux disease, mononucleosis, and allergies.

A sore throat can develop for many reasons including a viral or bacterial infection, or a common or seasonal allergy. Often associated with an infection, common or seasonal allergy includes some degree of nasal or sinus congestion. This congestion is typically referred to as post-nasal drip, in which mucous originating on the surface of the nasal mucosa or the sinus mucosa drains onto the upper esophagus. The accumulation of nasal mucosa in the upper esophagus also stimulates the swallowing reflex often associated with a sore throat. The swallowing reflex transports the acidic mucous into relatively constant contact with the region of the throat. The acidic nature of the mucous from the sinus mucosa or nasal mucosa erodes the epithelial tissue of the throat thereby exposing the underlying tissue to the acidic mucous. The nerve endings in the underlying tissue in contact with the acidic mucosa cause what one identifies as the discomfort or pain associated with a sore throat. The more inflamed the nasal mucosa or the sinus mucosa, the greater the production of the acidic mucous, the greater the erosion and the greater the severity of the pain and discomfort associated with the sore throat.

The pain of sore throat can be treated with various dosage forms or remedies. Common dosage forms include throat sprays, lozenges, and orally administered tablets or liquids, all of which may contain active ingredients. Sprays and lozenges typically contain topical analgesics or menthol to cool the pain of a sore throat. Orally administered tablets or liquids typically contain systemically acting active ingredients for pain, cough and/or cold; including, e.g., acetaminophen, NSAIDs, decongestants, and/or cough suppressants. In some cases, these products contain sensates for cooling which also help in alleviating pain or providing the perception of alleviating pain.

One of the main disadvantages of such products is lack of immediate effect and/or short duration. In many cases, sprays or liquids do not provide extended pain relief because the composition is swallowed almost immediately upon ingestion.

European Patent No. EP0506563B1 to PF Medicament, discloses a pharmaceutical composition in suspension form, that contains alginic acid, sodium bicarbonate and at least one thickening agent. The reference discloses that the composition is specifically intended for the treatment of gastroesophageal disorders related to gastroesophageal reflux.

WO2007110871 to Navaeh Pharma discloses pharmaceutical compositions and methods for treating, soothing or reducing the severity of a sore throat. The compositions comprise an oily vehicle which provides an oily coating to the throat of a subject; and an active ingredient in an amount effective to treat, sooth or reduce the severity of sore throat for an extended period of time.

U.S. Published Application No. 20040185093 discloses coating compositions for pharmaceutical dosage forms that contain a coating agent, a high intensity sweetener and a cooling agent. The reference discloses that the coating agent may be a film forming polymer, including, e.g., polyvinylalcohol (PVA), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethy-1 cellulose (HEMPMC), cellulose acetate (CA), cellulose acetate phthalate (CAP), carboxymethylcellulose (CMC), starches, and polymers and derivatives and mixtures thereof U.S. Published Application No. 20060062811 discloses pharmaceutical compositions that contain a non-volatile cooling agent, a cellulosic polymer and an aqueous vehicle. The reference discloses that the cellulosic polymer may include methylcellulose, hydroxypropylcellulose (HPC), hydroxyethylmethylcellulose (HEMC), hydroxypropylmethylcellulose (HPMC), hydroxybutylmethylcellulose (HBMC), cellulose acetate (CA), cellulose acetate phthalate (CAP), carboxymethylcellulose (CMC), hydroxyethylcellulose (HEC), hydroxythylethylcellulose (HEEC), hydroxyethylhydroxypropylmethyl cellulose (HEMPMC), and polymers, and derivatives and mixtures thereof. The reference further discloses that one suitable hydroxypropylmethylcellulose compound is "HPMC 2910", which is a cellulose ether having a degree of substitution of about 1.9 and a hydroxypropyl molar substitution of 0.23, and containing, based upon the total weight of the compound, from about 29% to about 30% methoxyl and from about 7% to about 12% hydroxypropyl groups and that HPMC 2910 is commercially available from the Dow Chemical Company under the tradename, "Methocel E" or "Methocel E5". The reference also discloses that another suitable microcrystalline cellulose is a dried coprecipitated microcrystal of cellulose and carboxymethyl cellulose and that sodium carboxymethyl cellulose is commonly used as the coprecipitate in microcrystalline cellulose. The reference further discloses microcrystalline cellulose such as that described is commercially available from FMC under the trademark, "Avicel™".

Tylenol® Daytime Severe Cold & Flu Liquid with Cool Burst; Tylenol® Cool Burst Daytime Cough & Sore Throat Reliever, and Tylenol® Cough & Sore Throat Nighttime Liquid, each of which first launched in 2004, contain active ingredient, citric acid, FD&C blue No. 1, flavors, polyethylene glycol, propylene glycol, purified water, sodium benzoate, sodium carboxymethylcellulose, sorbitol, sucralose, sucrose.

There remains a need for compositions and methods that are safe and effective to treat, soothe or reduce the severity of a sore throat. Such a composition should work quickly and provide superior sore throat relief for an extended period of time.

SUMMARY OF THE INVENTION

The present invention is directed to compositions that can be used to alleviate sore throat. The compositions, which provide a thin layer of coating on oral surfaces, enhance the sensory experience as compared to known compositions.

In accordance with an embodiment, the composition comprises a muco-adhesive material. Suitable muco-adhesive materials include gelling material, such as hydrocolloid, e.g., pectins, cellulosics, alginates, carrageenans, etc.

In an embodiment, the muco-adhesive material is a thickener. Suitable thickeners include, but are not limited to carboxymethylcellulose (CMC), microcrystalline cellulose and blends of CMC and microcrystalline cellulose, xanthan gum and konjac gum. Other thickeners include cellulosic polymers such as hypromellose, hydroxypropylcellulose and hdyroxyethylcellulose.

In accordance with an embodiment, the muco-adhesive material includes, but is not limited to, Avicel® BV 2219, Avicel® CL 611, Avicel-Plus® LM 310 stabilizer, 40% solids, Avicel® RC-591, Carbopol® 971P, Aqualon® CMC-7M8SF-PH, HPMC E4M and Nutricol® BV 5616.

The composition may contain from about 0.1 percent to about 3 percent muco-adhesive material. The composition may contain from about 0.5 percent to about 2 percent muco-adhesive material. These materials, which improve muco-adhesion, increase duration of relief.

In yet another embodiment, the composition further comprises a surface-active agent (also known as a surfactant). Suitable surfactants include polyoxyethylene-polyoxypropylene block copolymers. In an embodiment, the surfactant includes, but is not limited to, Lutrol® F68 or Kolliphor® P 188 (both poloxamer 188); Lutrol® F127 (poloxamer 407) and Tween® 80.

The composition may contain from about 0.05 percent to about 2 percent surfactant. The composition may contain from about 0.1 percent to about 1.5 percent surfactant. The composition may contain from about 0.5 percent to about 1 percent surfactant. The surfactant further enhances the perceived coating effect of the composition.

The resulting composition may be may be delivered as a spray or a liquid.

In an embodiment, the composition comprises an active ingredient.

In another embodiment, the composition comprises a sensate.

BRIEF DESCRIPTION OF THE DRAWINGS

FIG. 2 is a Stribeck curve for purified water. As can be seen from FIG. 2, the traction coefficient of water is relatively high.

FIG. 3 are Stribeck curves for samples C, F, and G, with and without active. A review of FIG. 3 shows that the traction coefficients formula G with API is, for the most part, outside of the desired range when tested in accordance with the method disclosed herein.

FIG. 4 is a viscosity plot for samples C, F, and G, with and without active.

FIG. 5 are Stribeck curves for samples C, F, and G compared to Nyquil®, Robitussin®, Mucinex® and Theraflu®. A review of FIG. 5 shows that the traction coefficients for Nyquil®, Robitussin®, Mucinex® and Theraflu® are outside of the desired range when tested in accordance with the method disclosed herein.

FIG. 6 are Stribeck curves for Tylenol® Cold and Flu Multi-Symptom Cool Burst, Motrin® and Sudafed®. A review of FIG. 6 shows that the traction coefficients for Tylenol® Cold and Flu Multi-Symptom Cool Burst, Motrin® and Sudafed® are outside of the desired range when tested in accordance with the method disclosed herein.

FIG. 7 is a viscosity plot for Children's Tylenol®, Children's Motrin®, Children's Benadryl®, Children's Sudafed® and Children's Imodium®.

FIG. 8 is a Stribeck curve for Tylenol® Cold and Flu Multi-Symptom Cool Burst. A review of FIG. 8 shows that the traction coefficient for Tylenol® Cold and Flu Multi-Symptom Cool Burst is outside of the desired range when tested in accordance with the method disclosed herein.

FIG. 9 are Stribeck curves for Tylenol® Cold and Flu Multi-Symptom Cool Burst placebo with 0.1% Lutrol® F 68; 0.3% Lutrol® F 68; 0.5% Lutrol® F 68; 0.5% Lutrol® F 127 and 0.5% Tween 80. (See also Table 2). FIG. 9 is discussed later in the specification.

FIG. 10 are Stribeck curves for Tylenol® Cold and Flu Multi-Symptom Cool Burst and Tylenol® Cold and Flu Multi-Symptom Cool Burst placebo with 0.1% Lutrol® F68; 0.3% Lutrol® F 68; 0.5% Lutrol® F 68; 0.5% Lutrol® F 127; and 0.5% Tween 80. (See also Table 2). FIG. 10 is discussed later in the specification.

FIG. 11 are Stribeck curves for samples J, K, L, M, N and O. A review of FIG. 11 shows that the traction coefficient for formulas L and N are outside the desired range when tested in accordance with the method disclosed herein. Given that the data in FIG. 11 for formulas L and N does not appear to match the data in Table 9, an error may have resulted in the curves for L and N in FIG. 11.

FIG. 12 is a Stribeck curve for Tylenol® placebo with 0.5% HPMC E4M. A review of FIG. 12 shows that the traction coefficient for Tylenol® placebo with 0.5% HPMC E4M is within the desired range when tested in accordance with the method disclosed herein.

FIG. 13 is a graph showing shear sweep of Tylenol® placebo with 0.5% HPMC E4M.

FIG. 14 is a graph showing shear sweep of Tylenol® placebo with 0.4% HPMC and Avicel® CL-611NF (0.25%, high shear).

FIG. 15 is a Stribeck curve for Tylenol® placebo with 0.4% HPMC and Avicel® CL-611NF (0.25%, high shear). A review of FIG. 15 shows that the traction coefficient for Tylenol® placebo with 0.4% HPMC and Avicel®

Figure 1:
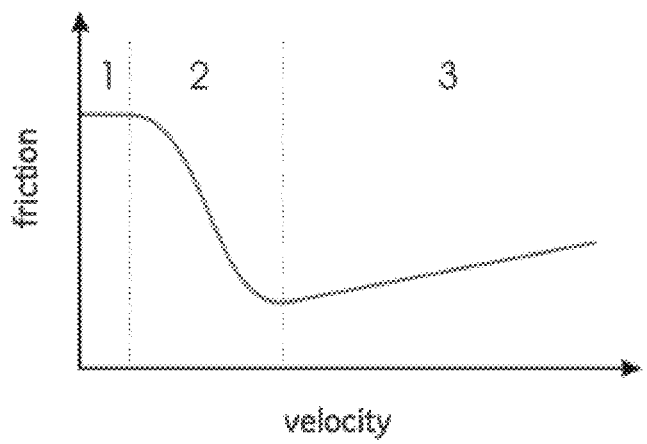
FIG. 1 is a schematic showing a Stribeck curve and how to assess the results on a Stribeck curve. Upon review of FIG. 1, one can see there are broadly three regimes. At very low velocity, there is no lubrication and there is the "high school" model of constant friction force. In region 2, "mixed friction", the lubrication is starting to have an effect. In region 3, "fluid friction", the lubrication dominates but viscous drag starts to be important. Most lubricants work by creating a fluid film between two solid surfaces, though solid film lubrication also exists. The thickness of the fluid film (a factor dependent on material properties, load, relative speed of the surfaces, temperature, and pressure) determines whether the lubricant is categorized as hydrodynamic, elasto-hydrodynamic, mixed, or boundary. The Stribeck curve is a tool used to break down which category a lubricant is functionally based on its viscosity, speed, and load.

CL-611NF (0.25%, high shear) is within the desired range when tested in accordance with the method disclosed herein.

FIG. 16 is a graph showing shear sweep for Tylenol® placebo with 0.4% HPMC, Kolliphor® P 188 (0.4%) and Avicel® CL-611NF (0.25%, high shear).

FIG. 17 is a Stribeck curve for Tylenol® placebo with 0.4% HPMC, Kolliphor® P 188 (0.4%) and Avicel® CL-611NF (0.25%, high shear). A review of FIG. 17 shows that the traction coefficient for Tylenol® placebo with 0.4% HPMC, Kolliphor® P 188 (0.4%) and Avicel® CL-611NF (0.25%, high shear) is within the desired range when tested in accordance with the method disclosed herein.

FIG. 18 is a graph showing shear sweep of Tylenol® placebo with Avicel® CL-611NF (2.0%).

FIG. 19 is a Stribeck curve for Tylenol® placebo with Avicel® CL-611NF (2.0%). A review of FIG. 19 shows that the traction coefficient for Tylenol® placebo with Avicel® CL-611NF (2.0%) is outside the desired range when tested in accordance with the method disclosed herein. Given that the data in FIG. 19 for this formula, which corresponds to formula A, does not appear to match the data in Table 5, an error may have resulted in the curve for this formula in FIG. 19.

FIG. 20 is a Stribeck curve for Tylenol® placebo with Avicel® CL-611NF (2.0%) and poloxamer 407 (0.25%). A review of FIG. 20 shows that the traction coefficient for Tylenol® placebo with Avicel® CL-611NF (2.0%) and poloxamer 407 (0.25%) is within the desired range. when tested in accordance with the method disclosed herein.

DETAILED DESCRIPTION OF INVENTION

It is believed that one skilled in the art can, based upon the description herein, utilize the present invention to its fullest extent. The following specific embodiments are to be construed as merely illustrative, and not as limiting the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

As used herein, the term "active ingredient" is used herein in a broad sense and may encompass any material that imparts a therapeutic effect. For example, the active ingredient can be a pharmaceutical, nutraceutical, vitamin, dietary supplement, nutrient, herb, foodstuff, dyestuff, nutritional, mineral, supplement, oral care agent or flavoring agent (sensate) or the like and combinations thereof.

"Dosage form" applies to any composition designed to contain a specific pre-determined amount (dose) of a certain ingredient, and for example, an active ingredient as defined herein. Suitable dosage forms may be pharmaceutical drug delivery systems and systems for delivering minerals, vitamins and other nutraceuticals, oral care agents, flavorants, and the like. In a particularly preferred embodiment, the dosage form is an orally administered system for delivering a pharmaceutical active ingredient to the gastro-intestinal tract of a human.

"Liquid dosage forms" may nonexclusively include suspensions or elixirs, wherein one or more of the active ingredients is dissolved, partially dissolved or in an undissolved or suspended state.

"Rheology" means the study of the flow of matter, primarily in a liquid state, but also as 'soft solids' or solids under conditions in which they respond with plastic flow rather than deforming elastically in response to an applied force. Rheology generally accounts for the behavior of non-Newtonian fluids, by characterizing the minimum number of functions that are needed to relate stresses with rate of change of strain or strain rates.

"Shear rheology" means the characterization of flow or deformation of a liquid originating from a simple shear stress field.

"Shear sweep" herein means the determination of the viscosity of a liquid at varied shear rates.

"Therapeutic effect," means any effect or action of an active ingredient intended to diagnose, treat, cure, mitigate, or prevent disease, or affect the structure or any function of the body.

"Traction" means the friction between a drive wheel and the surface it moves upon. It is the amount of force a wheel can apply to a surface before it slips. A wheel will have different traction on different surfaces; the coefficient of friction is based on pairs of surfaces.

"Traction coefficient" means internal fluid friction.

"Tribology" means the study of interacting surfaces in relative motion. It includes the study and application of the principles of friction and lubrication.

"Turbidity" means the cloudiness or haziness of a liquid or of a transparent solid.

"Stribeck curve" means a curve showing coefficient of friction and bearing number. Bearing number can be defined as sliding velocity, i.e., the relative sliding velocity of lubricant with viscosity per unit load.

"Viscosity" means the measure of a liquid's resistance to flow when the liquid is subjected to sheer stress.

The dosage form of the present invention preferably contains one or more active ingredients. Suitable pharmaceutical active ingredients include analgesics, anti-inflammatory agents, 'antiarthritics, anesthetics, antihistamines, antitussives, antibiotics, anti-infective agents, antipyretics, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, cough suppressants, decongestants, expectorants, oral contraceptives, diuretics, gastrointestinal agents, migraine preparations, motion sickness products, mucolytics, muscle relaxants, osteoporosis preparations, polydimethylsiloxanes, respiratory agents, sleep-aids, urinary tract agents, and pharmaceutically acceptable salts thereof, derivatives thereof, combinations thereof and mixtures thereof.

In accordance with an embodiment, the active ingredient is selected from acetyl salicylic acid, acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; and pharmaceutically acceptable salts thereof, derivatives thereof, combinations thereof and mixtures thereof.

Examples of useful NSAIDs include ibuprofen, naproxen, benoxaprofen, naproxen sodium, fenbufen, flurbiprofen, fenoprofen, fenbuprofen, ibuprofen, ketoprofen, indoprofen, pirprofen, carpofen, oxaprofen, pranoprofen, microprofen, tioxaprofen, suprofen, alminoprofen, tiaprofenic acid, fluprofen, bucloxic acid, celecoxib, and pharmaceutically acceptable salts thereof, derivatives thereof, combinations thereof and mixtures thereof.

Examples of cough and cold pharmaceutical active ingredients, which include antihistamines, cough suppressants, decongestants and expectorants, include, but are not limited to, bromopheniramine, carbinoxamine, acetylcysteine, guaifenesin, carbocysteine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, noscapine, clophedianol, menthol, benzonatate, ethylmorphone, codeine, acetylcysteine, carbocisteine, ambroxol, belladona alkaloids, sobrenol, guaiacol and cetirizine; and pharmaceutically acceptable salts thereof, derivatives thereof, combinations thereof and mixtures thereof.

In another embodiment, the at least one active ingredient is an NSAID and/or acetaminophen, and pharmaceutically acceptable salts thereof.

In an embodiment, the active ingredient is a topical analgesic such as benzocaine, benzydamine, dexpanthenol, menthol flurbiprofen or diclonene.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotidine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate, loperamide and racecadotril; glycopyrrolate; antiemetics, such as ondansetron, analgesics, such as mesalamine.

Examples of suitable polydimethylsiloxanes, which include, but are not limited to dimethicone and simethicone, as disclosed in U.S. Pat. Nos. 4,906,478, 5,275,822, and 6,103,260, the contents of each which is expressly incorporated herein by reference. As used herein, the term "simethicone" refers to the broader class of polydimethylsiloxanes, including but not limited to simethicone and dimethicone.

Suitable sensates include menthol, peppermint, mint flavors, fruit flavors, chocolate, vanilla, bubblegum flavors, coffee flavors, liqueur flavors and combinations and the like.

The a therapeutically effective amount of active ingredient or ingredients can readily be determined by one skilled in the art.

EXAMPLES

All tables are included separately as an attachment to this filing.

Batchelor et al., The application of tribology in assessing texture perception of oral liquids, Int. J. Pharmaceutics, 479 (2015) 277-281, discloses the use of tribology as a tool to understand properties of oral liquid medicines. Batchelor et al. defines tribology as "[the measure of] the friction between two interacting surfaces, in this case a steel ball on a silicone elastomer disk." The reference discloses that "[l]ubrication is often categorized by measuring the friction coefficient across a range of speeds as the extent of lubrication will vary. Often this data is presented as a Stribeck curve, which shows the traction coefficient as a function of speed of motion between surfaces. The Stribeck curve usually has three phases: 1. Boundary regime: where the speed is low, this measures the ability of the fluid to wet or adsorb to the surface and has in some cases been linked to astringency/grittiness (Rossetti et al., 2009) (high value of friction) and slipperiness/oiliness (low value of friction) (Malone et al., 2003; Prakash et al., 2013). 2. Mixed regime: where the speed is intermediate and the fluid present can partly separate the two rubbing surfaces. The friction coefficient reaches a minimum in this regime and typically lower values have been associated with creamy textures (Chojnicka-Paszun et al., 2012). 3. Hydrodynamic regime: where the speed is high and the fluid separates the surfaces; the film thickness and friction generated are dependent upon the viscosity of the food . . . . In terms of application of tribology to liquid medicines in the mouth we are mostly interested in low to intermediate speed movement (boundary/mixed regime as described above) to assess the ability of a medicine to coat the oral cavity as we hypothesize that a low-residue (non-coating) product is likely to be preferred and it is these regions that have previously been identified to be most relevant when considering oral processing (Malone et al., 2003)."

U.S. Pat. Nos. 8,342,032 and 8,413,481 to Cargill, Incorporated disclose the use of a tribology device to assess mouthfeel attributes of foods.

Example 1: Traction Coefficient Testing Procedure

A Mini Traction Machine (MTM2) from PCS Instruments, West London, UK was used to measure traction coefficient of liquid formulations. The instrument is designed to measure frictional properties of lubricated and unlubricated contacts under a wide range of rolling and sliding conditions. A 19.05 mm steel ball is in contact with 46 mm diameter silicone elastomer discs, which are independently driven to allow different relative motion (mixed rolling/sliding contact).

The frictional force between the ball and disc is measured by a force transducer. During testing this differential motion between the stainless-steel ball and polydimethylsiloxane (PDMS) disc causes the liquid samples to create a thin lubricating interface between the ball and the disc, and the degree of lubrication is measured in terms of frictional force measured by the force transducer. Measurements can be made at different temperature, slide to roll ratio, rolling speed and normal load applied by the ball on to the disc.

For current testing, Stribeck curves were generated by measuring traction coefficient at rolling speed from 1-15 mm/sec. Measurements were done at 37° C., a slide to roll ratio (SRR) of 50% and 2 N normal load. Each run consisted of 3 replicate measurements.

Traction coefficient has no units and is calculated by dividing the measured frictional force by the applied normal load (2 N for current testing).

Using this method, preferred traction coefficient for the liquid compositions of the invention is from about 0.001 to about 0.010 within 1-15 mm/sec. This includes, for example, measurements taken within 1-5 mm/sec, 5-10 mm/sec and/or 10-15 mm/sec.

Example 2 (Comparative): Measurement of Traction Coefficient for Commercial Products Several commercial products were analyzed for traction coefficient using the procedure in Example 1 at three different rolling speeds.

FIG. 5 includes Stribeck curves for Nyquil®, Robitussin®, Mucinex® and Theraflu®.

Table 1 summarizes the measured traction coefficient at 1-5, 5-10 and 10-15 mm/sec rolling speed for commercially available adult and pediatric formulations.

A review of FIG. 5 and Table 1 shows that the traction coefficients for Nyquil®, Robitussin®, Mucinex® and Theraflu® are outside of the desired range when tested in accordance with the method disclosed herein.

Example 3: Addition of Surfactant to Commercial Tylenol® Cold and Flu Multi-Symptom Cool Burst Product To improve the lubricity of commercial formulations, surfactants can be added to the formulations by mixing in a suitable laboratory vessel at approximately 50 RPM using a laboratory mixer until dispersed. Table 2 summarizes the effect of the addition of surfactant on the commercially available Tylenol® Cold and Flu Multi Symptom Cool Burst product.

FIG. 9 includes Stribeck curves for Tylenol® Cold and Flu Multi-Symptom Cool Burst placebo with 0.1% Lutrol® F 68; 0.3% Lutrol® F 68; 0.5% Lutrol® F 68; 0.5% Lutrol® F 127 and 0.5% Tween 80.

FIG. 10 includes Stribeck curves for Tylenol® Cold and Flu Multi-Symptom Cool Burst and Tylenol® Cold and Flu Multi-Symptom Cool Burst placebo with 0.1% Lutrol® F68; 0.3% Lutrol® F 68; 0.5% Lutrol® F 68; 0.5% Lutrol® F 127; and 0.5% Tween 80. The addition of surfactant shows the reduction of traction coefficient as compared to the sample without surfactant.

A review of FIG. 9 and Table 2 shows that at all concentrations studied, the traction coefficient for Lutrol® F 68 is, for the most part, within the desired range, wherein the traction coefficient for Lutrol® 127 and Tween 80 are, for the most part, outside of the desired range, when tested in accordance with the method disclosed herein.

A review of FIG. 10 and Table 2 shows that the traction coefficient for the Tylenol® Cold and Flu Multi-Symptom Cool Burst placebo is not only outside of the desired range, but also significantly higher than the traction coefficients for the formulas tested, when tested in accordance with the method disclosed herein.

Example 4: Addition of Muco-Adhesive Material to Placebo Liquid Formulations

The following placebo (i.e., without active ingredient) formulations were prepared by first adding purified water to a suitable vessel. Muco-adhesive material was then added while mixing. For formulations A and B, a high shear mixer was used to dissolve/activate the muco-adhesive material followed by addition of propylene glycol while mixing using a propeller mixer at about 500-1000 RPM. The rest of the ingredients were added and mixed at approximately 500-1000 RPM for at least 30 minutes. For formulation C, muco-adhesive material is dissolved in purified water using a propeller mixer at approximately 500 RPM. After complete dissolution, the solution was heated using a water bath to a temperature between 140°-170° C. for 15 minutes while continuously stirring. The solution was cooled to room temperature before adding propylene glycol while mixing. The rest of the ingredients were added and mixed for at least 30 minutes. The formulations are shown in Table 3, and the tribology data is shown in Table 5.

A review Table 5 shows that for the most part the traction coefficients for formulas A-C are within the desired range when tested in accordance with the method disclosed herein.

Example 5: Addition of Muco-Adhesive Material to Liquid Formulations Containing Active Pharmaceutical Ingredient (API)

The following formulations were prepared by adding purified water to a suitable vessel. The muco-adhesive material was then added while mixing. For formulation D, a high shear mixer was used to dissolve/activate the muco-adhesive material followed by addition of propylene glycol while mixing using a propeller mixer at about 500-1000 RPM. The rest of the ingredients were added and mixed at approximately 50-100 RPM for at least 30 minutes. For formulation E, muco-adhesive material is dissolved in purified water, using a propeller mixer at approximately 500 RPM. After complete dissolution, the solution was heated using a water bath to a temperature between 140°-170° C. for 15 minutes while continuously stirring. The solution was cooled to room temperature before adding propylene glycol while mixing. The rest of the ingredients were added and mixed for at least 30 minutes. The formulations are shown in Table 4 and the tribology data is shown in Table 5.

A review Table 5 shows that for the most part the traction coefficients for formulas D and E are within the desired range when tested in accordance with the method disclosed herein.

Example 6: Formulations with Muco-Adhesive Material and/or Surfactant

Additional placebo formulations were prepared to evaluate the addition of various muco-adhesive materials and/or surfactants to liquid formulations. These formulations were prepared by adding purified water to a suitable vessel. The muco-adhesive material was then added while mixing at approximately 500 RPM until hydrated. Propylene glycol was then added while mixing. The rest of the ingredients, including surfactant, were added and mixed at approximately 500-1000 RPM for at least 30 minutes. The formulations are shown in Table 6, Table 7 and Table 8 and the tribology data is shown in Table 9.

A review of Table 9 shows that, for the most part, the traction coefficient is outside the desired range for formulas F, G and H and within the desired range for formulas I-S, when tested in accordance with the method disclosed herein.

Example 7: Turbidity and Rheology Measurements

The turbidity was measured for several formulas in Examples 4 and 6; and the rheology was measured for several commercial formulas and formulas in Examples 4 and 6. The data is shown in tables 10 (Turbidity) and 11 (Rheology).

Part A: Turbidity Procedure

Turbidity measurements were carried out using Turbiscan Lab Expert. Two different synchronous optical sensors received the light transmitted through and backscattered by samples at an angle of 180° and 45° with respect to the incident radiation, respectively. The two sensors scanned the entire height (~45 mm) of the samples. Experimental data were correlated in percentage to the light flux of two reference standards constituted by a polystyrene latex suspension (absence of transmission and maximum backscattering) and a silicon oil (maximum transmission and absence of backscattering). Table 10 shows the % of light transmitted through the sample and detected by the detector at of 180° to the incident light.

A review of Table 10 shows that Formulas A and P are opaque with low light transmission; Formulas B and O are translucent with slightly better light transmission; and formulas Q and C are transparent with high light transmission.

Part B: Rheology (Viscosity) Procedure

Viscosity data presented in Table 11 shows a snapshot of measured viscosity at various shear rates. Measurement was carried out using a TA Instruments-AR2000 Rheometer using a parallel plate configuration.

Shear Sweep

All tests were performed using a TA Instruments AR2000 rheometer with a 60 mm parallel plate geometry with gap setting of 0.5 mm. Measurement temperature of 25° C. was maintained with a Peltier plate for all the samples. The rheometer was mounted on a vibration-isolated platform and leveled. Samples were loaded without air bubbles and excess sample was "trimmed" from the edges when the gap was 10% larger than the desired gap. Shear sweep experiments were run to with shear rates ranging from 0.001 to 100 l/s.

Example 8: Sensory Testing of Formulations Containing Active Ingredients

The following samples were taste-tested for sensory notes as compared to commercially available Tylenol® Cold liquid (control).

| Sample Number | Sample Description | Notes on Sensory Observations |
|---|---|---|
| Example 4, Formula C | | Commenter: More viscous than sample F. More coating effect than F.<br>Commenter 2: Thicker than F. |
| Example 5, Formula D | Opaque blue liquid | Commenter 1: Creamy texture, coating sensation in the mouth with residual flavor remaining after 4-5 mins. Mint flavor was not too strong.<br>Commenter 2: Creamy and silky mouthfeel. Appears to leave a long lasting (5 minutes plus) cooling sensation in the throat well after the liquid is gone. Good minty flavor. |
| Example 5, Formula E | Translucent blue liquid | Commenter 1: Sample appeared more viscous than G but less creamy in texture The sample did coat the mucosa and had a stronger mint taste<br>Commenter 2: thicker than control and F. No unique mouthfeel features like in G. Strong minty flavor. Slight coating but impact of extended sensation in the throat was low. |
| Example 5, Formula F | Clear blue liquid | Commenter 1: Sample had a smooth texture although not as creamy as sample G. Sample was less viscous (thick) than sample C and did not have the same mouth coating effect as either C or G.<br>Commenter 2: Slightly thicker than control but less thick than C. No unique mouthfeel characteristics. Good minty flavor. No longer lasting cooling feeling in the throat vs placebo. |
| Example 6, Formula G | | Commenter 1: Less viscous, but more creamy in texture, than E. More creamy in texture than F. Mouth coating effect.<br>Commenter 2: Unique mouth features. Cooling sensation appeared to linger in the mouth. |
| Tylenol® Cold and Flu Multi-Symptom Cool Burst Product | Clear blue liquid | Commenter 1: Thin liquid with strong mint flavor and a very limited sense of coating the oral cavity<br>Commenter 2: Thin - typical of most OTC liquids. Little coating action in the mouth and throat. Good cool sensation, but it did not linger like other samples, especially G. |

Example 9—Taste Test

Consumer Use Study

Greater muco-adhesion of liquids in the throat is a highly desirable consumer benefit. Liquid placebo formulations were provided to consumers to assess their sensory and muco-adhesive properties compared to a placebo that represented a currently sold liquid formula.

Products were pre-dispensed (10 ml) and handed out by a moderator for participant visual evaluation and product usage experience. Participants were instructed to take a bite or more of an unsalted cracker and a sip of room temperature bottled water to cleanse the palate between product trials.

Randomized product evaluations. Visual assessment followed by ingestion.

Products were pre-dispensed in a dosage cup (volume of 10 ml.) and handed out by a moderator.

Consumers were instructed to eat unsalted saltines and drink water to cleanse the palate.

This was repeated for all 4 products.

A fifth product (194) was only assessed visually, in a bottle, not a dosage cup.

The prototypes were all placebos, and were referenced as:
- 359 Control Tylenol® Cold & Mucus Severe (see Table 1 and Table 2)
- 673 Translucent Avicel® BV 2219 and Poloxamer 188 (Example 0) (See Table 8 and Table 9)
- 784 Translucent Avicel® BV 2219 (Example B) (see Table 3 and Table 5)
- 458 Transparent sample Nutricol BV 5616 (Example C) (See Table 3 and Table 5)
- 194 Opaque sample Avicel CL 611 (Example A, B) (See Table 3 and Table 5)

The two prototypes that were considered to be similar in viscosity were 673 and 784. Their thicker viscosities were considered to be unique, and because they targeted specific areas in the mouth and throat, consumers felt they would be appropriate for a sore throat or cough calming medication.

The difference between 673 and 784 was that sensations from 673 were felt more in the throat versus 784 which was felt more/only in the mouth. Additionally, the cooling sensation from 673 lasted longer, and was thought to be a benefit for a sore throat/cough calming product.

The thin viscosity of the control (359) was easy to swallow and was similar to other OTC liquids that consumers are used to. In addition, it had a broader spectrum of sensory feeling felt from the nose/sinuses through the chest and further down, making it more of a multi-symptom medication.

A viscosity between the control (359) and prototypes 673/784 could potentially provide multi-symptom relief, yet have unique targeted muco-adhesive properties.

The least liked prototype was 458. It was not fluid, and was perceived to be similar to gelatin because it swallowed as a "solid glob". Also, there was minimal to no sensation felt, since it went straight to the stomach without affecting the mouth, throat or chest.

| Control (359) | Prototype (673) | Prototype (784) | Prototype (458) |
| --- | --- | --- | --- |
| Thin viscosity | Medium viscosity | Medium viscosity | Too thick viscosity |
| Broader sensory feeling | Sensation felt in throat | Sensation felt in mouth | No sensation |
| Multi-symptom relief | Targeted relief | Targeted relief | No relief |

Consumers experienced a cooling sensation with the control product (359) and prototype (673).

This cooling sensation for 673 was long lasting and well liked. This was considered to be a significant difference versus current products, and an advantage for a cough/cold/sore throat medication.

It was frequently described as a sensation experienced when they breathed in they could feel the cooling sensation in the back of throat and sinuses.

Observations on 359
  The thinner viscosity was easiest to swallow.
  The control was considered to be a multi-symptom medication, and less effective for sore throat because it was less coating.
  Taste was strong and more like medicine, but minty, cool, fresh and refreshing like mouthwash.

Observations on 673
  Although minty taste comments were made, this was the only product that had comments about sweet, syrupy or sugary flavors.
  There were several mentions of aspartame or a diet sugar substitute.
  The sensation was felt in the back of the mouth and down into the throat. It seemed to stop at the bottom of the throat.
  The sensation was described as cooling and coating,
  This formula was thought to be a good option for a sore throat medication.
  There was also some sensation of initial cooling then warming, likened to Icy Hot.
  The consistency was thought to be in between 359 and 784

Observations on 784
  The appearance was described as thick and cloudy, it gave the impression that it would coat the throat
  The taste was described as a typical medicine, but the minty peppermint flavor was pleasant.
  Additionally, the flavor was thought to be a bit milder and less like menthol than 673.
  However, the viscosity made it difficult to get the product out of the dosage cup, and there was enough residue that remained in the cup that consumers felt they would need to try again in order to get a full dose. This was thought to be wasteful or an unnecessary hassle.
  The coating and experience was more concentrated in the mouth, on the tongue, roof of mouth, and surrounding/coating teeth and back of throat.
  This prototype was thought to be a good formula for a sore throat medication.
  Any sensation did not last as long as 359 or 673.

Observations on 458
  The appearance gave the impression it would be too thick and difficult to swallow, partially because of the visible bubbles. It was likened to Jello.
  The viscosity for prototype 458 was considered to be:
  Too thick
  Difficult to swallow
  Unpleasant feeling in the mouth
  Swallowed as a solid, not liquid
  Went down as a glob, similar to a Jello shot
  Did not leave any sensations in the mouth, throat or chest
  Sensation, if any, was tingling and limited to lips, gums and roof of mouth.
  There was little flavor associated with this product because it was swallowed so quickly.

Observations on 194
  The viscosity for prototype 194 was considered to be very thick, opaque, and likely difficult to swallow.
  When the bottle was manipulated and turned upside down, the contents were coating the walls and dripping slowly. This gave consumers the impression that it would coat the throat.
  Consumers noticed that the product was not uniform, based on a thinner layer of liquid at the top, and expected it would need to be shaken before dosing.
  The opaque appearance was described as:
  Cloudy
  Murky
  Slimy
  Dirty
  Blue Pepto Bismol
  Overall, the appearance was not appealing to consumers.

The foregoing examples are not intended to limit the scope of the present invention, which may be set out in the claims. Various equivalents and substitutions will be recognized by those skilled in the art in view of the foregoing disclosure and these are contemplated to be within the scope of the invention.

TABLE 1

Traction Coefficient Measurements of Commercial Products

| Commercially available product[1] | Traction Coefficient 1-5 mm/sec rolling speed | | | Traction Coefficient 5-10 mm/sec rolling speed | | | Traction Coefficient 10-15 mm/sec rolling speed | | |
|---|---|---|---|---|---|---|---|---|---|
| | Min | Max | Average | Min | Max | Average | Min | Max | Average |
| Nyquil ® | 0.0541 | 0.2486 | 0.1241 | 0.02605 | 0.07505 | 0.052375 | 0.01205 | 0.041 | 0.028855 |
| Theraflu ® | 0.01926 | 0.0711 | 0.04154 | 0.0133 | 0.033886 | 0.020286 | 0.009 | 0.01953 | 0.013839 |
| Mucinex ® | 0.034525 | 0.098775 | 0.05886 | 0.014075 | 0.044 | 0.02655 | 0.01295 | 0.01675 | 0.015413 |
| Tylenol ®Cold and Flu Multi Symptom Cool Burst | 0.028767 | 0.45543 | 0.21339 | 0.0081 | 0.055933 | 0.023477 | 0.004833 | 0.0179 | 0.008633 |
| Children's Tylenol ® | 0.041325 | 0.072875 | 0.05855 | 0.025225 | 0.0456 | 0.032888 | 0.022025 | 0.029175 | 0.02845 |
| Children's Motrin ® | 0.015375 | 0.0231 | 0.01852 | 0.0126 | 0.019125 | 0.016617 | 0.01165 | 0.018125 | 0.014463 |
| Children's Sudafed ® | 0.0135 | 0.19575 | 0.09883 | 0.00265 | 0.009375 | 0.00685 | 0.00185 | 0.004325 | 0.002525 |

[1]Ingredients for each product appear in a later table in this document.

TABLE 2

Tylenol Cold and Flu with Surfactant Addition

| | Traction Coefficient 1-5 mm/sec rolling speed | | | Traction Coefficient 5-10 mm/sec rolling speed | | | Traction Coefficient 10-15 mm/sec rolling speed | | |
|---|---|---|---|---|---|---|---|---|---|
| | Min | Max | Avg | Min | Max | Avg | Min | Max | Avg |
| Tylenol ® Cold and Flu Multi-symptom Cool Burst[1] | 0.028767 | 0.45543 | 0.21339 | 0.0081 | 0.055933 | 0.023477 | 0.004833 | 0.0179 | 0.008633 |
| Tylenol ® Cold and Flu Multi-symptom with 0.1% Lutrol ® F68 (Poloxamer ® 188)[2] | 0.0005 | 0.002333 | 0.00162 | 0.0009 | 0.001733 | 0.001252 | 0.000767 | 0.002033 | 0.001523 |
| Tylenol ® Cold and Flu Multi-symptom with 0.3% Lutrol ® F68 (Poloxamer ® 188) | 0.0013 | 0.006 | 0.00362 | 0.000967 | 0.0027 | 0.001875 | 0.000867 | 0.002033 | 0.00149 |
| Tylenol ® Cold and Flu Multi-symptom with 0.5% Lutrol ® F68 (Poloxamer ® 188) (H) | 0.0022 | 0.033133 | 0.01006 | 0.001433 | 0.004933 | 0.002819 | 0.001267 | 0.002533 | 0.001907 |
| Tylenol ® Cold and Flu Multi-symptom with 0.5% Lutrol ® F127 (Poloxamer ® 407) (P)[3] | 0.004867 | 0.016567 | 0.00974 | 0.003333 | 0.011333 | 0.00701 | 0.0044 | 0.008533 | 0.00681 |
| Tylenol ® Cold and Flu Multi-symptom with 0.5% Tween 80 (G)[4] | 0.0075 | 0.037233 | 0.01894 | 0.009833 | 0.022367 | 0.018008 | 0.009667 | 0.0194 | 0.014833 |

[1]Ingredients in % w/w: propylene glycol 27.7477; sorbitol solution (70%) 18.4958; glycerin 7.3994; flavor 0.6012; sodium benzoate 0.185; sucralose 0.1344; anhydrous citric acid 0.0462; FD&C Blue #1 0.0015; purified water QS.
[2]Polyoxyethylene-polyoxypropylene block co-polymer, commercially available from BASF Corporation.
[3]Polyoxyethylene-polyoxypropylene block co-polymer, commercially available from BASF Corporation.
[4]Polyoxyethylene(20)sorbitan monooleate.

TABLE 3

Muco-adhesive Material in Placebo Liquid Formulations

| Ingredients: | Formula A % W/W | Formula B % W/W | Formula C % W/W |
|---|---|---|---|
| Propylene Glycol[1] | 27.7477 | 27.7477 | 27.7477 |
| Sorbitol Solution (70%) | 18.4958 | 18.4958 | 18.4958 |
| Glycerin | 7.3994 | 7.3994 | 7.3994 |
| Flavor[2] | 0.6012 | 0.6012 | 0.6012 |
| Sodium Benzoate | 0.185 | 0.185 | 0.185 |
| Sucralose | 0.1344 | 0.1344 | 0.1344 |
| Anhydrous Citric Acid | 0.0462 | 0.0462 | 0.0462 |
| FD&C Blue #1 | 0.0015 | 0.0015 | 0.0015 |
| Avicel CL 611[3] | 2.0 | 0 | 0 |
| Avicel BV 2219[4] | 0 | 1 | 0 |
| Nutricol BV 5616[5] | 0 | 0 | 0.2 |
| Purified Water | QS | QS | QS |

[1]Viscous, colorless liquid with faintly sweet taste used as a solvent.
[2]International Flavors and Fragrances Cooler No. 2, CAS #: 220621-22-7.
[3]Microcrystalline cellulose and sodium carboxymethylcellulose, commercially available from FMC Corporation.
[4]Sodium carboxymethylcellulose, microcrystalline cellulose and calcium chloride, commercially available from FMC Corporation.
[5]Xanthan gum and Konjac flour, commercially available from the FMC Corporation.

TABLE 4

Formulations with API:

| Ingredients: | Formula D % W/W | Formula E % W/W |
|---|---|---|
| Propylene Glycol | 27.7477 | 27.7477 |
| Sorbitol Solution (70%) | 18.4958 | 18.4958 |
| Glycerin | 7.3994 | 7.3994 |
| Flavor[6] | 0.6012 | 0.6012 |
| Sodium Benzoate | 0.185 | 0.185 |
| Sucralose | 0.1344 | 0.1344 |
| Anhydrous Citric Acid | 0.0462 | 0.0462 |
| FD&C Blue #1 | 0.0015 | 0.0015 |
| Microcrystalline Cellulose (Avicel Plus ® LM 310 stabilizer, 40% solids)[7] | 0 | 0 |
| Avicel BV 2219 | 1 | 0 |
| Nutricol BV 5616 | 0 | 0.2 |
| Acetaminophen | 2.004 | 2.004 |

TABLE 4-continued

Formulations with API:

| Ingredients: | Formula D % W/W | Formula E % W/W |
|---|---|---|
| Guaifenesin | 1.2332 | 1.2332 |
| Dextromethorphan HBr | 0.0617 | 0.0617 |
| Phenylephrine HCl | 0.0308 | 0.0308 |
| Purified Water | 41.0564 | 41.8564 |

[6]International Flavors and Fragrances Cooler No. 2, CAS #: 220621-22-7.
[7]Commercially available from FMC Corporation.

TABLE 5

Traction Coefficient Analysis

| | Traction Coefficient 1-5 mm/sec rolling speed | | | Traction Coefficient 5-10 mm/sec rolling speed | | | Traction Coefficient 10-15 mm/sec rolling speed | | |
|---|---|---|---|---|---|---|---|---|---|
| | Min | Max | avg | Min | Max | avg | Min | Max | avg |
| Placebo Formula A | 0.0015 | 0.0244 | 0.00711 | 0.0009 | 0.003067 | 0.001925 | 0.001 | 0.0025 | 0.002087 |
| Placebo Formula B | 0.002133 | 0.008033 | 0.00416 | 0.0021 | 0.006267 | 0.003894 | 0.002833 | 0.004833 | 0.004043 |
| Placebo Formula C | 0.004433 | 0.019 | 0.00871 | 0.0035 | 0.011867 | 0.007354 | 0.004733 | 0.009633 | 0.007137 |
| Formula D with API | 0.001625 | 0.002775 | 0.00252 | 0.00155 | 0.002925 | 0.002138 | 0.002025 | 0.0025 | 0.002025 |
| Formula E with API | 0.00165 | 0.004025 | 0.00265 | 0.000975 | 0.0025 | 0.002175 | 0.000975 | 0.002625 | 0.0018 |

TABLE 6

Formulations of Carbopol and Poloxamer Additions

| Ingredients: | Formula F Placebo % W/V | Formula G Placebo with 0.5% tween 80 % W/V | Formula H Placebo with 0.5% Lutrol F 68 % W/V | Formula I Placebo with 0.5% Carbopol % W/V | Formula J Placebo with 0.5% Carbopol + 1% Tween 80 % W/V |
|---|---|---|---|---|---|
| Propylene Glycol | 30 | 30 | 30 | 30 | 30 |
| Sorbitol Solution (70%) | 20 | 20 | 20 | 20 | 20 |
| Glycerin | 8 | 8 | 8 | 8 | 8 |
| Sodium Benzoate | 0.2 | 0.2 | 0.2 | 0.2 | 0.2 |
| Sucralose | 0.145 | 0.145 | 0.145 | 0.145 | 0.145 |
| Anhydrous Citric Acid | 0.05 | 0.05 | 0.05 | 0.05 | 0.05 |
| Carbopol 971 P[8] | 0 | 0 | 0 | 0.5 | 0.5 |
| Lutrol F 68 (Poloxamer 188) | 0 | 0 | 0.5 | 0 | 0 |
| Tween 80 | 0 | 0.5 | 0 | 0 | 1 |
| Purified Water | QS | QS | QS | QS | QS |

[8]Carboxypolymethylene polymer, commercially available from Lubrizol Corporation.

TABLE 7

Additional Formulas with Carboxymethylcellulose and Microcrystalline Cellulose

| Ingredients: | Formula K Placebo with 0.5% CMC + 0.5% Avicel-RC591 % W/V | Formula L Placebo with 0.5% CMC + 0.5% Avicel RC591 + 0.5% Lutrol F68 % W/V | Formula M Placebo with 1.0% CMC + 0.5% Avicel-RC591 % W/V | Formula N Placebo with 1.0% CMC + 0.5% Avicel RC591 + 0.5% Lutrol F68 % W/V |
|---|---|---|---|---|
| Propylene Glycol | 30 | 30 | 30 | 30 |
| Sorbitol Solution (70%) | 20 | 20 | 20 | 20 |
| Glycerin | 8 | 8 | 8 | 8 |
| Sodium Benzoate | 0.2 | 0.2 | 0.2 | 0.2 |
| Sucralose | 0.145 | 0.145 | 0.145 | 0.145 |
| Anhydrous Citric Acid | 0.05 | 0.05 | 0.05 | 0.05 |

TABLE 7-continued

Additional Formulas with Carboxymethylcellulose and Microcrystalline Cellulose

| Ingredients: | Formula K Placebo with 0.5% CMC + 0.5% Avicel-RC591 % W/V | Formula L Placebo with 0.5% CMC + 0.5% Avicel RC591 + 0.5% Lutrol F68 % W/V | Formula M Placebo with 1.0% CMC + 0.5% Avicel-RC591 % W/V | Formula N Placebo with 1.0% CMC + 0.5% Avicel RC591 + 0.5% Lutrol F68 % W/V |
|---|---|---|---|---|
| Avicel RC591[9] | 0.5 | 0.5 | 0.5 | 0.5 |
| Aqualon ® CMC-7M8SF-PH[10] | 0.5 | 0.5 | 1 | 1 |
| Lutrol F 68 (Poloxamer 188) | 0 | 0.5 | 0 | 0.5 |
| Purified Water | QS | QS | QS | QS |

[9]Microcrystalline cellulose and carboxymethylcellulose sodium, commercially available from FMC Biopolymer Corporation.
[10]Carboxymethylcellulose, commercially available from Ashland Specialty Ingredients.

TABLE 8

Additional formulas with Avicel, HPMC

| Ingredients: | Formula O Placebo with 1% Avicel BV 2219 + 0.5% Lutrol F 68 % W/V | Formula P Placebo with 1.8% Avicel CL 611 + 0.5% Lutrol F127 % W/V | Formula Q Placebo with 0.5% HPMC E4M % W/V | Formula R Placebo with 0.4% HPMC E4M + 0.25% Avicel CL 611 % W/V | Formula S with 0.4% HPMC E4M + 0.25% Avicel CL 611 + 0.4% Poloxamer 188 % W/V |
|---|---|---|---|---|---|
| Propylene Glycol | 30 | 30 | 30 | 30 | 30 |
| Sorbitol Solution (70%) | 20 | 20 | 20 | 20 | 20 |
| Glycerin | 8 | 8 | 8 | 8 | 8 |
| Sodium Benzoate | 0.2 | 0.2 | 0.2 | 0.2 | 0.2 |
| Sucralose | 0.145 | 0.145 | 0.145 | 0.145 | 0.145 |
| Anhydrous Citric Acid | 0.05 | 0.05 | 0.05 | 0.05 | 0.05 |
| Avicel BV 2219 | 1.0 | 0 | 0 | 0 | 0 |
| Avicel CL 611 | 0 | 1.8 | 0 | 0.25 | 0.25 |
| Lutrol F 68 (Poloxamer 188) | 0.5 | 0 | 0 | 0 | 0.4 |
| Lutrol F 127 | 0 | 0.5 | 0 | 0 | 0 |
| HPMC E4M[11] | 0 | 0 | 0.5 | 0.4 | 0.4 |
| Purified Water | QS | QS | QS | QS | QS |

[11]Hydroxypropylmethylcellulose with viscosity in the range of 2,700 to 5,400 cps and particle size of 170-250 micrometers, available from Ashland Specialty Group.

TABLE 9

Tribology Data for Additional Formulas

| | Traction Coefficient 1-5 mm/sec rolling speed | | | Traction Coefficient 5-10 mm/sec rolling speed | | | Traction Coefficient 10-15 mm/sec rolling speed | | |
|---|---|---|---|---|---|---|---|---|---|
| | Min | Max | Avg | Min | Max | Avg | Min | Max | Avg |
| Formula F | 0.116667 | 0.5254 | 0.32526 | 0.018367 | 0.128533 | 0.046165 | 0.0034 | 0.020967 | 0.012217 |
| Formula G with 0.5% Tween 80 | 0.0075 | 0.037233 | 0.01894 | 0.009833 | 0.022367 | 0.018008 | 0.009667 | 0.0194 | 0.014833 |
| Formula H with 0.5% Lutrol F 68 | 0.011967 | 0.0469 | 0.02539 | 0.008867 | 0.027767 | 0.016175 | 0.0058 | 0.016067 | 0.010733 |
| Formula I with 0.5% Carbopol 971 P | 0.006467 | 0.037167 | 0.01542 | 0.003633 | 0.008433 | 0.005619 | 0.003333 | 0.004333 | 0.0037 |
| Formula J with 0.5% Carbopol 971 P + 1% Tween 80 | 0.002433 | 0.005133 | 0.00349 | 0.001667 | 0.004267 | 0.00259 | 0.001867 | 0.0028 | 0.00231 |

TABLE 9-continued

Tribology Data for Additional Formulas

| | Traction Coefficient 1-5 mm/sec rolling speed | | | Traction Coefficient 5-10 mm/sec rolling speed | | | Traction Coefficient 10-15 mm/sec rolling speed | | |
|---|---|---|---|---|---|---|---|---|---|
| | Min | Max | Avg | Min | Max | Avg | Min | Max | Avg |
| Formula K with 0.5% CMC + 0.5% Avicel-RC591 | 0.0078 | 0.047467 | 0.02174 | 0.004733 | 0.014 | 0.009323 | 0.005033 | 0.008167 | 0.006657 |
| Formula L with 0.5% CMC + 0.5% Avicel-RC591 + 0.5% Lutrol F 68 | 0.000667 | 0.001867 | 0.00129 | 0.000833 | 0.002233 | 0.001742 | 0.0014 | 0.002833 | 0.001997 |
| Formula M with 1.0% CMC + 0.5% Avicel-RC591 | 0.001633 | 0.027933 | 0.00682 | 0.001367 | 0.003267 | 0.002188 | 0.001267 | 0.0031 | 0.002163 |
| Formula N with 1.0% CMC + 0.5% Avicel-RC591 + 0.5% Lutrol F68 | 0.0004 | 0.002667 | 0.00148 | 0.001333 | 0.0026 | 0.002096 | 0.001833 | 0.003133 | 0.0024 |
| Formula O with 1.0% Avicel BV 2219 + 0.5% Lutrol F68 | 0.0019 | 0.004867 | 0.00328 | 0.001667 | 0.003333 | 0.002585 | 0.0018 | 0.002767 | 0.002233 |
| Formula P with 1.8% Avicel CL 611 + 0.5% Lutrol F127 | 0.002167 | 0.0051 | 0.00331 | 0.0015 | 0.003567 | 0.002444 | 0.002233 | 0.003367 | 0.00263 |
| Formula Q with 0.5% HPMC E4M | 0.001 | 0.0036 | 0.00197 | 0.0013 | 0.0026 | 0.001679 | 0.001233 | 0.0024 | 0.001787 |
| Formula R with 0.4% HPMC E4M + 0.25% Avicel CL611 | 0.000167 | 0.002333 | 0.00151 | 0.001 | 0.002633 | 0.001627 | 0.0013 | 0.002 | 0.00164 |
| Formula S with 0.4% HPMC E4M + 0.25% Avicel CL 611 + 0.4% Poloxamer 188 | 0.0027 | 0.0078 | 0.0046 | 0.002367 | 0.0064 | 0.004185 | 0.002667 | 0.0064 | 0.004117 |

TABLE 10

Turbidity Data:

| Formulation | Visual Appearance | Transmission |
|---|---|---|
| Formula A with Avicel CL 611 | Opaque | 0.01259 |
| Formula P with Avicel CL 611 and Poloxamer 188 | Opaque | 0.01644 |
| Formula B with 1% Avicel BV 2219 | Translucent | 0.9 |
| Formula O | Translucent | 1.36 |
| Formula Q with HPMC E4M | Transparent | 91.9074 |
| Formula C with Nutricol BV 5616 | Transparent | 78.9579 |

TABLE 11

Rheology Data

| | Viscosity at different shear rates (PaS) | | |
|---|---|---|---|
| | 0.1 1/S | 1 1/s | 10 1/s |
| Delsym ®[12] | 0.2553 | 0.217 | 0.09861 |
| Nyquil ®[13] | 0.04401 | 0.01891 | 0.02048 |
| Theraflu ®[14] | 0.03394 | 0.02073 | 0.01923 |
| Mucinex ®[15] | 0.2952 | 0.2206 | 0.09435 |
| Tylenol ® Cold and Flu Multi Symptom Cool Burst Formula[16] | 0.01044 | 0.00966 | 0.00757 |
| Children's Tylenol ®[17] | 8.132 | 1.983 | 0.4929 |
| Children's Motrin ®[18] | 4.514 | 1.632 | 0.4306 |
| Children's Sufafed ®[19] | 0.04856 | 0.03386 | 0.03292 |
| Formula C with Nutricol BV 5616 | 0.4518 | 0.3668 | 0.2724 |
| Formula B with Avicel BV 2219 | 36.91 | 4.144 | 0.5608 |
| Formula A with Avicel CL 611 | 16.61 | 4.972 | 0.1726 |

TABLE 11-continued

Rheology Data

| | Viscosity at different shear rates (PaS) | | |
|---|---|---|---|
| | 0.1 1/S | 1 1/s | 10 1/s |
| Formula H with 0.5% Poloxamer 188 | 0.0199 | 0.00127 | 0.00444 |
| Formula F | 0.0127 | 0.00143 | 0.00246 |

[12] Active Ingredient: Acetaminophen 650 mg/20 ml, Dextromethorphan HBr 20 mg/20 ml, Phenylephrine 10 mg/20 ml, Guaifenesin 400 mg/20 ml. Inactive Ingredients: Anhydrous Citric Acid, FD & C Blue 1, FD & C Red 40, Flavors, Glycerin, Propylene Glycol, Propyl Gallate, Edetate Sodium, Purified water, Sodium Benzoate, Trisodium Citrate dihydrate, Sucralose, Sorbitol Solution, Xanthan Gum.
[13] Nyquil contains Acetamninphen 325 mg, Dextromethorphan 15 mg, Doxylamine succinate 6.25 mg; acesulfame potassium, alcohol, citric acid, FD&C Blue No. 1, FD&C Red No. 40, flavor, high fructose corn syrup, polyethylene glycol, propylene glycol, purified water, saccharin sodium, sodium citrate.
[14] Theraflu contains Acetaminophen (650 mg), Diphenhydramine HCl (25 mg), Phenylephrine HCl (10 mg), Acesulfame Potassium, Alcohol, Anhydrous Citric Acid, Edetate Disodium, FD&C Blue No. 1, FD&C Red No. 40, Flavors, Glycerin, Maltitol Solution, Propylene Glycol, Purified Water, Sodium Benzoate, Sodium Citrate.
[15] Mucinex contains Acetaminophen (650 mg), Guaifenesin (400 mg), Phenylephrine HCl (10 mg) (Nasal Decongestant), Anhydrous Citric Acid, Edetate Disodium, FD&C Blue #1, FD&C Red #40, Flavors, Glycerin, Propyl Gallate, Propylene Glycol, Purified Water, Sodium Benzoate, Sorbitol, Sucralose, Trisodium Citrate Dihydrate (May contain this ingredient), Xanthan Gum.
[16] Ingredients listed in Table 2.
[17] Active Ingredient: Acetaminophen 160 mg/5 ml. Inactive Ingredients: Anhydrous Citric Acid, Butyl paraben, FD & C Red 40, Flavors, Glycerin, High Fructose Corn Syrup, Microcrystalline Cellulose and Caboxymethylcellulose sodium, Propylene glycol, Purified water, Sodium Benzoate, Sorbitol Solution, Sucralose, Xanthan gum.
[18] Active Ingredient: Ibuprofen 100 mg/5 ml. Inactive Ingredients: Anhydrous Citric Acid, Acesulfame Potassium, D & C Yellow 10, Polysorbate 80, Pregelatinized Starch, FD & C Red 40, Flavors, Glycerin, Purified Water Sodium Benzoate, Sucrose, Xanthan gum.
[19] Active Ingredient: Dextromethorphan HBr 5 mg/5 ml, Phenylephrine 2.5 mg/5 ml. Inactive Ingredients: Anhydrous Citric Acid, FD & C Blue 1, FD & C Red 40, Flavors, Glycerin, Caboxymethylcellulose sodium, Edetate Sodium, Purified water, Sodium Benzoate, Sodium Citrate, Sucralose, Sorbitol Solution.

The invention claimed is:

1. A liquid composition for treating cough or cold symptoms, wherein said liquid composition comprises between about 0.1% and 3.0% of a mucoadhesive material, wherein said mucoadhesive material is a hydroxypropylmethylcellulose, and wherein said liquid composition further comprising from about 0.1% and 1.5% surfactant and wherein said surfactant comprises poloxamer 188, wherein said liquid composition has a traction coefficient of less than about 0.01 at 1-15 mm/sec rolling speed at 37° C., a slide to roll ratio (SRR) of 50% and 2 N normal load.

2. The liquid composition of claim 1, further comprising an active ingredient.

3. The liquid composition of claim 2, wherein the active ingredient is an analgesic.

4. The liquid composition of claim 2, wherein the active ingredient is selected from the group consisting of acetaminophen, dextromethorphan, guaifenesin, ibuprofen and phenylepherine.

5. The liquid composition of claim 2, wherein the active ingredient comprises acetaminophen.

6. The liquid composition of claim 1, wherein the composition comprises a sensate.

7. The liquid composition of claim 1, wherein said liquid composition further comprising a second mucoadhesive material.

8. The liquid composition of claim 7, wherein the second mucoadhesive material comprises microcrystalline cellulose and sodium carboxymethyl cellulose.

9. A method of alleviating a symptom selected from the group consisting of cough, nasal congestion and sore throat in a subject comprising administering to a subject in need thereof the composition of claim 1.

10. The method of claim 9, wherein the symptom is sore throat.

11. The method of claim 9, wherein said liquid composition has a traction coefficient of from about 0.001-0.010 at 1-15 mm/sec rolling speed when tested in accordance with the method disclosed herein.

* * * * *